US009701986B2

(12) United States Patent
Camu et al.

(10) Patent No.: US 9,701,986 B2
(45) Date of Patent: *Jul. 11, 2017

(54) MICROBIAL COMPOSITION FOR THE FERMENTATION OF COCOA MATERIAL

(75) Inventors: Nicholas Camu, Lebbeke-Wieze (BE); Herwig Bernaert, Lebbeke-Wieze (BE); Tobias Lohmueller, Lebbeke-Wieze (BE)

(73) Assignee: BARRY CALLEBAUT AG, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/387,567

(22) PCT Filed: Jul. 29, 2010

(86) PCT No.: PCT/EP2010/061043
§ 371 (c)(1),
(2), (4) Date: Jan. 27, 2012

(87) PCT Pub. No.: WO2011/012680
PCT Pub. Date: Feb. 3, 2011

(65) Prior Publication Data
US 2012/0128823 A1 May 24, 2012

(30) Foreign Application Priority Data
Jul. 29, 2009 (EP) .................... 09166780

(51) Int. Cl.
*A23G 1/28* (2006.01)
*A23G 1/02* (2006.01)
*A23G 1/30* (2006.01)
*C12N 1/20* (2006.01)
*C12N 1/16* (2006.01)
*C12P 1/02* (2006.01)
*A23G 1/00* (2006.01)
*C12N 1/18* (2006.01)
*C12P 1/04* (2006.01)
*C12P 39/00* (2006.01)
*C12R 1/02* (2006.01)
*C12R 1/225* (2006.01)
*C12R 1/25* (2006.01)
*C12R 1/865* (2006.01)

(52) U.S. Cl.
CPC .............. *C12P 1/02* (2013.01); *A23G 1/002* (2013.01); *A23G 1/02* (2013.01); *C12N 1/16* (2013.01); *C12N 1/18* (2013.01); *C12N 1/20* (2013.01); *C12P 1/04* (2013.01); *C12P 39/00* (2013.01); *C12R 1/02* (2013.01); *C12R 1/225* (2013.01); *C12R 1/25* (2013.01); *C12R 1/865* (2013.01)

(58) Field of Classification Search
CPC ........... A23G 1/002; A23G 1/02; C12N 1/16; C12N 1/18; C12N 1/20

USPC ..................... 426/45, 62, 631, 655
See application file for complete search history.

(56) References Cited

U.S. PATENT DOCUMENTS

| | | |
|---|---|---|
| 3,003,388 A | 10/1961 | Hunter et al. |
| 4,435,436 A | 3/1984 | Terink et al. |
| 4,704,292 A | 11/1987 | Kattenberg et al. |
| 4,784,866 A | 11/1988 | Wissgott et al. |
| 6,403,133 B1 | 6/2002 | Barfuss et al. |
| 2003/0215558 A1 | 11/2003 | Kealy et al. |
| 2008/0193595 A1 | 8/2008 | De Vuyst et al. |
| 2008/0268133 A1 | 10/2008 | Kealey et al. |
| 2009/0130284 A1* | 5/2009 | Miller et al. ............. 426/541 |
| 2012/0196001 A1 | 8/2012 | Camu et al. |
| 2013/0029007 A1 | 1/2013 | Bernaert et al. |

FOREIGN PATENT DOCUMENTS

| | | |
|---|---|---|
| EP | 0187415 | 7/1986 |
| EP | 0614613 | 9/1994 |
| GB | 653240 | 5/1951 |
| GB | 751121 | 6/1956 |
| GB | 2059243 | 4/1981 |
| GB | 2182538 | 5/1987 |
| GB | 2241146 | 8/1991 |
| JP | S59224653 | 12/1984 |
| JP | 06090666 | 4/1994 |

(Continued)

OTHER PUBLICATIONS

Galvez, S. L. et al. 2007. Study on the microflora and biochemistry of cocoa fermentation in the Dominican Republic. Int. J. Fd. Microbiol. 114: 124-130.*
Endo, A. et al. International J. System. Evolution. Microbiol., 57: 708-712 (2007).*
"Acetobacter syzygii gene for 16S rRNA, strain: 9H-2," retrieved from EBI accession No. EM_PRO:AB052712, Database accession No. AB052712, 2002.
"Acetobacter tropicalis 16S rRNA gene, strain LMG 1663," retrieved from EBI accession No. EM_PRO:AJ419842, Database accession No. AJ419842, 2002.
"Acetobacter syzygii strain A265 16S ribosomal RNA gene, partial sequence," retrieved from EBI accession No. EM_PRO:DQ523496, Database accession No. DQ523496, 2006.

(Continued)

*Primary Examiner* — Hamid R Badr
(74) *Attorney, Agent, or Firm* — Hoxie & Associates LLC

(57) ABSTRACT

The invention relates to the use of a microbial composition for regulating the fermentation of such materials, in particular using compositions comprising specific combinations of microorganisms including at least three *Lactobacillus* species and a yeast species. The present invention further relates to a method for regulating fermentation of cocoa material, such as beans and/or pulp by using a microbial composition as defined herein, and to the fermented cocoa material thereby obtained. The invention also relates to the use of the obtained fermented cocoa material for the preparation of cocoa products and products derived therefrom, including chocolate. The present invention further relates to a method for downstream processing of cocoa beans that have been fermented with a microbial composition as defined herein, and to the downstream products thereby obtained.

20 Claims, 3 Drawing Sheets

(56) References Cited

FOREIGN PATENT DOCUMENTS

| | | |
|---|---|---|
| JP | 7016059 | 1/1995 |
| WO | WO 98/09533 A1 | 3/1998 |
| WO | WO 2007/031186 | 3/2007 |
| WO | WO 2007/140770 | 12/2007 |
| WO | WO2009/093030 | 7/2009 |
| WO | WO2010/104926 | 9/2010 |
| WO | WO 2011/012680 | 2/2011 |

OTHER PUBLICATIONS

"Acetobacter tropicalis strain A77 16S ribosomal RNA gene, partial sequence," retrieved from EBI accession No. EM_PRO: DQ523494, Database accession No. DQ523494, 2006.

Ardhana, et al. "The Microbial Ecology of Cocoa Bean Fermentations in Indonesia," *International Journal of Food Microbiology*, vol. 86, Nos. 1-2, pp. 87-99, 2003.

Bernaert, H., "The nutritional aspects of chocolate," *Food Science and Technology Today*, vol. 20, No. 4, 2006.

Bhumibhamon, et al., "Cocoa Fermentation III: Improvement of Cocoa Fermentation by Inoculated with Selected Mixed Culture in Laboratory and Farm Trial," Kasetsart Journal: Natural Science (Thailand), vol. 31, pp. 327-341, 1997.

Bhumibhamon, et al., "Cocoa Fermentation IV: Chemical Properties and Sensory Evaluation in Mix-Culture Fermented Cocoa," Kasetsart Journal: Natural Science (Thailand), vol. 31, pp. 419-428, 1997.

Bhumibhamon, et al., "Cocoa Fermentation: Study of Microbiological, Physical and Chemical Changes during Cocoa Fermentation," Kasetsart Journal: Natural Science (Thailand), vol. 31, 1997.

Bhumibhamon, et al., "Cocoa Fermentation I: Identification and Metabolites Study of Natural Cocoa Fermentation Microorganisms," Kasetsart Journal: Natural Science (Thailand), vol. 31, 1997.

Bhumibhamon, et al., "Cocoa Fermentation II: Effect of Enzyme Pectinase on Natural Cocoa Fermentation," Kasetsart Journal: Natural Science (Thailand), vol. 31, 1997.

Holt, et al., "The Shorter Bergey's Manual of Determinative Biology, $8^{th}$ ed." pp. 94-95 and 218-222, 1977.

Lagunes Galvez, et al., "Study on the microflora and biochemistry of cocoa fermentation in the Dominican Republic," *International Journal of Food Microbiology*, Elsevier Science Publi., Amsterdam, NL, vol. 114, No. 1, pp. 124-140, 2007.

Samah, et al., "Fermentation Products in Cocoa Beans Inoculated with Acetobacter xylinum," Asean Food Journal, vol. 8, No. 1, pp. 22-25, 1993.

Tomlins, K. et al., "Effects of fermentation and drying practices on the chemical and physical profiles of Chana cocoa," *Food Chemistry*, vol. 46, No. 3, pp. 257-263, 1993.

Bispo, E.S. et al., "Alkalinization Process for Cocoa (*Theobroma cacao* L.) Nibs and Quality Evaluation of the Powder by Response Surface Methodology", *J. Food Sci. Technol.*, 2002, vol. 39, No. 1, pp. 14-20.

Camu, Nicholas et al., "Dynamics and Biodiversity of Populations of Lactic Acid Bacteria and Acetic Acid Bacteria Involved in Spontaneous Heap Fermentation of Cocoa Beans in Ghana", *Applied and Environmental Microbiology*, Mar. 2007, vol. 73, No. 6, pp. 1809-1824, XP-002605871.

"Cocoa beans—specification", International Standard ISO 2451, First edition—Dec. 15, 1973, pp. 1-3, XP008132456.

Kakao aus Neuguinea, XP008132425, p. 297.

Schwan, Rogane F. et al., "Critical Reviews in Food Science and Nutrition", *The Microbiology of Cocoa Fermentation and Its Role*, 2004, vol. 44, Nr. 4, pp. 205-221.

Schwan, Rosane Freitas, "Cocoa Fermentations Conducted with a Defined Microbial Cocktail Inoculum", *Applied and Environmental Microbiology*, Apr. 1998, vol. 64, No. 4, pp. 1477-1483.

S. Tagro Guehi, et. al., "Effects of Turning Beans and Fermentation Method on the Acidity and Physical Quality of Raw Cocoa Beans" *Advanced Journal of Food Science and Technology*, vol. 2, Issue 3, pp. 163-171, 2010.

International Search Report dated Jan. 2, 2007 for International Application No. PCT/EP2006/008377.

Bibliographic Data of JPS59224653, Meiji Seika Co, "Treatment for Improving Taste and Flavor of Cacao Beans or its Processed Product", 1984, Espacenet (English version of Abstract).

ADM Cocoa International, de Zaan Cocoa and Chocolate Manual, $40^{th}$ Anniversary Edition (2009).

International Search Report for International Application No. PCT/EP2010/061043, (published Mar. 31, 2011).

\* cited by examiner

MICROBIAL COMPOSITION FOR THE FERMENTATION OF COCOA MATERIAL

CROSS REFERENCE TO RELATED APPLICATIONS

This application is a United States National Stage application under 35 USC §371 of PCT/EP2010/061043, filed Jul. 29, 2010, which claims priority to EP 09166780.8, filed Jul. 29, 2009, the contents of each of which are incorporated herein by reference.

FIELD OF THE INVENTION

The invention relates to the field of fermentation of cocoa material, such as cocoa beans and/or cocoa pulp. The invention relates to the use of a microbial composition for regulating the fermentation of such materials, in particular using compositions comprising specific combinations of microorganisms including at least three *Lactobacillus* species. The present invention further relates to a method for regulating fermentation of cocoa material, such as beans and/or pulp and to the fermented cocoa material thereby obtained. The invention also relates to the use of the obtained fermented cocoa material for the preparation of cocoa products and products derived there from, including chocolate.

BACKGROUND OF THE INVENTION

Cocoa beans are the principal raw material for chocolate production. These seeds are derived from the fruit pods of the tree *Theobroma cacao*, which is cultivated in plantations in the equatorial zone, e.g., in Ivory Coast, Ghana, and Indonesia. The cocoa beans are embedded in a mucilaginous pulp inside the pods. Raw cocoa beans have an astringent, unpleasant taste and flavour, and have to be fermented, dried, and roasted to obtain the desired characteristic cocoa flavour and taste. The chocolate flavour is influenced by the origin of the cocoa beans, the cocoa cultivar, the on-the-farm fermentation and drying process, and the roasting and further processing performed by the chocolate manufacturer.

After removal of the beans from the pods, the first step in cocoa processing for example for the cocoa variety Forastero is a spontaneous 6 to 10-day fermentation of beans and pulp in heaps, boxes, baskets, or trays. During such process, the beans are freed from adhering pulp. At the end of this period the decomposed pulp is generally washed away by water and the beans dried to produce the cocoa beans of commerce.

A microbial succession of yeasts, lactic acid bacteria (LAB), and acetic acid bacteria (AAB) takes place during fermentation. The yeasts depectinise the pulp and produce ethanol from sugars and citric acid under anaerobic conditions in an acid, carbohydrate-rich environment. As more pulp is drained away, more ethanol is produced and both temperature and pH increase, creating ideal conditions for the growth of LAB and AAB. LAB convert sugars and organic acids into lactic acid. As more air is coming in, AAB start to develop and oxidize the ethanol initially produced by the yeasts to acetic acid. Ethanol and acetic acid diffuse into the beans and this, in combination with the heat produced by this exothermic bioconversion, causes the death of the seed embryo. This in turn initiates biochemical changes in the beans leading to the formation of precursor molecules for the development of a characteristic aroma, flavour, and colour of the beans. These properties are further developed during drying, roasting, and final processing of well-fermented cocoa beans. The activity of yeast, LAB, and AAB is thus essential for the production of high-quality cocoa.

However, the spontaneous cocoa fermentation process is very inhomogeneous and suffers from great variations in both microbial counts and species composition and hence metabolites. The variations seem to depend on many factors including country, farm, pod ripeness, post-harvest pod age and storage, pod diseases, type of cocoa, variations in pulp/bean ratio, the fermentation method, size of the batch, season and weather conditions, the turning frequency or no turning, the fermentation time, etc. which makes reproducibility of fermentation particularly difficult. Because the uncontrolled nature of the usual fermentation process, particularly with respect to the lack of control over the growth and development of microorganisms and metabolic production during the process, the quality of the finished cocoa beans is variable.

Attempts have been made in the prior art to control fermentation parameters.

For instance, WO 2007/031186 discloses a method to regulate the fermentation of plant material consisting of cocoa beans and/or cocoa pulp by adding to said plant material specific bacterial cultures containing at least one lactic acid bacterium and/or at least one acetic acid bacterium at different time points during the fermentation process.

GB 2 059 243 describes a process for the fermentation of cocoa beans with the consecutive use of a pectinolytic yeast and an acetic acid bacterium in an aqueous medium, with agitation and aeration. GB 2 241 146 deals with the mechanical depulping of the cocoa beans before fermentation.

Schwan (1998, Appl Environ Microbiol 64: 1477-83) and Schwan & Wheals (2004, Critical Reviews in Food Science 44: 205-221) disclose the use of starter cultures in cocoa bean fermentation and specifically refer to an inoculum consisting of the strains *Saccharomyces cerevisiae* var. *chevalieri*, *L. lactis*, *L. plantarum*, *Acetobacter aceti* and *Gluconobacter oxydans* subsp. *Suboxydans*, while Samah et al. (1993, Asean Food Journal, Asean Food Handling Bureau, Kuala Lumpur, MY, vol. 8, no. 1, pg. 22-25) discloses the use of *Acetobacter xylinum* as inoculum during the fermentation of cocoa beans.

Bhumibhamon et al. (1997a, Kasetsart J. Nat. Science 31:327-341) and Bhumibhamon et al. (1997 b, Kasetsart J. Nat. Science 31:419-428) both refer to the use of specific starter cultures for improving cocoa fermentation. A preferred culture mentioned in Bhumibhamon et al. (1997a) comprises for instance *Saccharomyces chevalieri*; *Saccharomyces cerevisiae* and *Acetobacter aceti*.

However, fermentation parameters remain difficult to control in prior art methods and industry must therefore address a wide variability in the composition of a batch of processed cocoa beans. Taste problems may occur such as the presence of (too much) acids, a lack of cocoa taste, and too much off-flavour. Therefore, there remains a need in the art for further controlling fermentation processes of cocoa beans in order to obtain cocoa beans having more consistent or improved characteristics, such as highly flavoured cocoa beans of good and reproducible quality. There also remains a need in the art for a reproducible method of fermenting cocoa materials.

SUMMARY OF THE INVENTION

The present invention aims to provide improved microbial compositions for controlling fermentation of cocoa materials.

In a first aspect, the invention relates to the use of a microbial composition for regulating fermentation of plant material essentially consisting of beans and/or pulp derived from fruit pods of the species *Theobroma cacao*, wherein said composition comprises at least three *Lactobacillus* species and at least one *Acetobacter* species. More in particular, the invention relates to the use of a microbial composition comprising:

*Lactobacillus plantarum*, *Lactobacillus fermentum*, and *Acetobacter pasteurianus*, at least one additional *Lactobacillus* species selected from the group consisting of *Lactobacillus parafarraginis*, *Lactobacillus farraginis*, *Lactobacillus diolivorans*, *Lactobacillus faeni* and *Lactobacillus paracasei*, and at least one strain of a yeast species of a genus chosen from the group consisting of *Saccharomyces* and *Candida*.

In a preferred embodiment, the invention relates to the use of a microbial composition as defined herein wherein said yeast species is *Saccharomyces cerevisiae*.

In another embodiment, the invention relates to the use of a microbial composition as defined herein, wherein said composition is a starter culture or a high density culture, comprising at least $10^2$ CFU (colony forming units) of bacterial strains per g plant material.

In another aspect, the invention relates to a method for regulating fermentation of plant material essentially consisting of beans and/or pulp derived from fruit pods of the species *Theobroma cacao*, said method comprising adding to the plant material a microbial composition as defined herein.

In yet another aspect, the invention relates to fermented plant material essentially consisting of beans and/or pulp derived from fruit pods of the species *Theobroma cacao*, and preferably fermented cocoa beans, obtained or obtainable by carrying out the method according to the invention.

In another aspect, the invention relates to the use of fermented cocoa beans according to the invention for the preparation of cocoa products selected from the group comprising or consisting of cocoa nibs, cocoa powder, cocoa extract, cocoa liquor, cocoa mass, cocoa flakes, cocoa butter, and cocoa cake. The invention also relates to a cocoa product selected from the group comprising or consisting of cocoa nibs, cocoa powder, cocoa extract, cocoa liquor, cocoa mass, cocoa butter and cocoa cake, prepared with one or more fermented cocoa beans according to the invention.

Unexpectedly, the beans that were fermented using a microbial composition according to the invention showed a light-breaking effect. This means that the fermented beans obtained by carrying out the present fermentation process, have a lighter colour than conventionally fermented cocoa beans (which are browner).

In a preferred embodiment, the present invention therefore provides fermented cocoa beans, and particularly fermented cocoa beans in the form of a powder or cocoa liquor, having an L* value higher than 14, e.g., higher than 15, preferably higher than 16, e.g., higher than 17, more preferably higher than 18, and for instance and very preferably higher than 19 or higher than 20, such as for example having an L* value between 14 and 20, preferably between 16 and 20, more preferably between 17 and 20 or between 18 and 20 such as between 18 and 19.

In another preferred embodiment, the present invention further provides a cocoa product as defined above, and particularly cocoa product in the form of a powder or cocoa liquor, having an L* value higher than 14, e.g., higher than 15, preferably higher than 16, e.g., higher than 17, more preferably higher than 18, and for instance and very preferably higher than 19, or higher than 20, such as for example having an L* value between 14 and 20, preferably between 16 and 20, more preferably between 17 and 20 or between 18 and 20 such as between 18 and 19.

As explained elsewhere in this specification, the microbial compositions, methods and uses described herein allow to obtain beans of a non-Java origin which when fermented have a colour comparable to or approaching the colour of Java origin beans, which are known to have a light colour (e.g., have L* value higher than 20). Consequently, in embodiments the fermented cocoa beans or cocoa products, particularly in the form of a powder or cocoa liquor, having L* values as specified above are of non-Java origin.

More particularly, it is known that Java origin beans are commonly obtained from *Theobroma cacao* subsp. *cacao* clones DR2, DRC16, ICRRI01 or ICRRI02. Hence, in embodiments the fermented cocoa beans or cocoa products, particularly in the form of a powder or cocoa liquor, having L* values as specified above are not from (i.e., are other than) *Theobroma cacao* subsp. *cacao* clones DR2, DRC16, ICRRI01 and ICRRI02, and optionally hybrids thereof.

Accordingly, the microbial compositions, methods and uses as disclosed herein may be particularly suited and employed for producing fermented cocoa beans or cocoa products, particularly in the form of a powder or cocoa liquor, which have L* value as specified above or which display a light-breaking effect. For example, the microbial compositions, methods and uses as disclosed herein may be employed for increasing the L* value of fermented cocoa beans or cocoa products, particularly in the form of a powder or cocoa liquor.

More generally, the microbial compositions, methods and uses as disclosed herein allow to control, modulate or steer the L* value of fermented cocoa beans or cocoa products, particularly in the form of a powder or cocoa liquor. In particular, by allowing to produce lighter or light-breaking beans as a starting material, the downstream processing steps (e.g., degree of roasting, amount of water in the roaster, etc.) may be adapted to achieve a wide range of L* values (e.g., L* values between 4 and 21) of cocoa products, such as cocoa powder, cocoa liquor or even chocolate. The present microbial compositions, methods and uses allow for this flexibility in controlling the L* value of cocoa beans and cocoa products such as cocoa powder, liquor or chocolate, without having to resort to using bean blends including highly expensive Java origin beans.

Beans of non-Java origin which when fermented have a colour comparable to or approaching the colour of Java origin beans as obtainable using the microbial starter compositions described herein, and cocoa products derived there from such as cocoa powder or liquor, also allow to produce chocolate or chocolate products which may have composition typical of "dark" chocolate but nevertheless having comparably lighter colour which is more desirable with many consumers.

Accordingly, the microbial compositions, methods and uses as disclosed herein and cocoa beans fermented thereby may be particularly suited and employed for increasing the L* value of chocolate comprising dry solids made of said cocoa beans.

More generally, as explained above the microbial compositions, methods and uses as disclosed herein allow to control, modulate or steer the L* value of fermented cocoa beans or cocoa products, particularly in the form of a powder or cocoa liquor, and thereby also allow to control, modulate or steer the L* value of chocolate comprising dry solids made of said cocoa beans or products.

Also provided is thus light-coloured chocolate comprising dry cocoa solids. Particularly, said dry cocoa solids are of non-Java origin (i.e., are derived or prepared from cocoa beans of non-Java origin). More particularly, said dry cocoa solids are not from (i.e., are other than) *Theobroma cacao* subsp. *cacao* clones DR2, DRC16, ICRRI01 and ICRRI02, and optionally hybrids thereof. Preferably, said chocolate does not comprise dry milk solids, i.e., the chocolate is dark chocolate. Also preferably, the chocolate comprises 35% w/w or more dry cocoa solids (i.e., including cocoa butter and dry non-fat cocoa solids), e.g., 40% w/w or more, preferably 45% w/w or more, e.g., 50% w/w or more, more preferably 60% w/w or more, e.g., 70% w/w or more, even more preferably 80% w/w or more, e.g., 85% or 90% or 95% w/w or more dry cocoa solids Whereas the chocolate may have L* value between 4 and 21, preferably and without limitation the chocolate may have L* value higher than 14, e.g., higher than 15, preferably higher than 16, e.g., higher than 17, more preferably higher than 18, and for instance and very preferably higher than 19, or higher than 20, such as for example having an L* value between 14 and 20, preferably between 16 and 20, more preferably between 17 and 20 or between 18 and 20 such as between 18 and 19.

Downstream chocolate products comprising, consisting essentially of or consisting of said chocolate are also disclosed.

Further, as shown in the examples section and particularly substantiated by Tables 4 and 4a the microbial compositions, methods and uses taught herein allow to produce fermented cocoa beans having particularly advantageous characteristics demonstrable by a cut test, more specifically having certain comparably low fractions of slaty and/or defective beans and/or certain comparably high fractions of purple beans as determined by a cut test.

Hence, also disclosed herein are fermented cocoa beans characterised in that they contain:
(a) less than 3% slaty beans, preferably less than 2% slaty beans, more preferably 1% or less slaty beans, such as between 0 and 1% slaty beans; and/or
(b) less than 3% defective beans, preferably less than 2% defective beans, more preferably 1% or less defective beans, such as between 0 and 1% defective beans; and/or
(c) more than 11% purple beans, e.g., more than 12, 13 or 14% purple beans, preferably 15% or more purple beans, such as 20% or more purple beans, more preferably 30% or more purple beans such as 40% or more purple beans, and optionally up to 45% or up to 50% or up to 60% purple beans. The purple beans are fully fermented. Particularly, the beans may be non-Java origin beans or non-Java clones, as elucidated elsewhere in this specification.

One shall appreciate that when cocoa beans are defined herein by the fraction thereof having a given characteristic, the recitation of cocoa beans may particularly refer to a plurality of cocoa beans, such as to a population, collection or set of cocoa beans, such as for example and without limitation to a sample or test set of between 50 and 500 beans, or between 100 and 300 beans.

Particularly disclosed are fermented cocoa beans characterised by at least the above characteristic (a) or at least the above characteristic (c), or characterised by the combination of the above characteristics (a) and (b), or preferably (a) and (c), or (b) and (c), or preferably (a) and (b) and (c).

Said fermented cocoa beans may be additionally characterised in that they contain:

(d) less than 3% mouldy beans, preferably less than 2% mouldy beans, more preferably 1% or less mouldy beans, such as between 0 and 1% mouldy beans; and/or
(e) less than 3% broken beans, preferably less than 2% broken beans, more preferably 1% or less broken beans, such as between 0 and 1% broken beans; and/or
(f) less than 3% germinated beans, preferably less than 2% germinated beans, more preferably 1% or less germinated beans, such as between 0 and 1% germinated beans.

As also set forth in the examples section, the inventors realised that beans fermented as taught herein allow for numerous improvements in the downstream processing of the beans.

Accordingly, the microbial compositions, methods and uses as disclosed herein may be particularly suited and employed for producing fermented cocoa beans or cocoa products which improve the efficiency of processing of the beans or products, such as in particular increase speed of micronising, winnowing, mixing, roasting, cooling, grinding and/or liquor pressing.

Summarised, the Applicants have shown that using the particular starter cultures as defined herein in the fermentation of cocoa material has a significant effect on the speed of fermentation, and on the quality, appearance, nutritional and organoleptic properties and/or downstream processing efficiency of the fermented beans and chocolate produced thereof. For instance, it was shown by the Applicants that using the herein disclosed specific starter cultures levels of polyphenols in general and epicatechin in particular in the fermented beans were conserved, and thus their degradation was prevented or reduced in the cocoa products and chocolate products derived there from. Polyphenols in general and epicatechin in particular are known to be antioxidants and to have health promoting effects, e.g. promoting heart health.

The Applicants thus provide a way of regulating a natural, unpredictable fermentation process into a well-controlled process, initiated by the addition of a microbial starter culture as defined herein, leading to faster and improved fermentation. Use of the present microbial compositions not only allows to speed up the fermentation process but also to influence the quality, taste and/or appearance of the obtained fermented beans and cocoa product or chocolate products derived there from. Moreover, faster fermentation processes provide important beneficial effects, as they allow carrying out controlled cocoa fermentation on a much larger scale to obtain higher production capacities, which are necessary to comply with increasing demands for cocoa.

Another particular beneficial effect of fermenting the beans using a microbial composition as defined herein is that it permits to yield fermented beans of a relative uniform and reproducible quality.

In another aspect, the invention provides a method for the downstream processing of cocoa beans that have been fermented with a microbial composition as defined herein.

In an embodiment, the invention provides a method for producing a red or purple cocoa-derived material from fermented beans, comprising the steps of:
a) providing cocoa beans that have been fermented with a microbial composition as defined herein
b) preparing a cocoa-derived material from the fermented beans of step a), and
c) treating the cocoa-derived material of step b) with an acid or with an aqueous acidic solution wherein said cocoa-derived material is selected from the group comprising or consisting of cocoa nibs, cocoa flakes, cocoa cake, cocoa powder, cocoa liquor and chocolate. Preferably, said cocoa-derived material is cocoa nibs or cocoa liquor.

The present invention also relates to red or purple cocoa-derived material obtained from cocoa beans that have been fermented with a microbial composition as defined herein wherein said cocoa-derived material is selected from the group comprising or consisting of cocoa nibs, cocoa flakes, cocoa cake, cocoa powder, cocoa liquor and chocolate, and preferably is cocoa nibs or cocoa liquor. Preferably said red or purple cocoa-derived material is obtained or obtainable by carrying out a method as described herein.

The invention further relates to the use of fermented cocoa beans according to the invention for the preparation of food products, preferably chocolate products. In another embodiment the invention is directed to a food product, preferably a chocolate product, prepared with one or more fermented cocoa beans according to the invention and/or with one or more cocoa products according to the invention. It shall be clear that during the downstream processing of fermented cocoa beans to food products such as chocolate products, the fermented beans may be subjected to downstream treatment steps, such as those defined in this application.

With the insight to better show the characteristics of the invention, some preferred embodiments and examples are described hereafter referring to the enclosed drawings.

DESCRIPTION OF THE INVENTION

Figure 1:
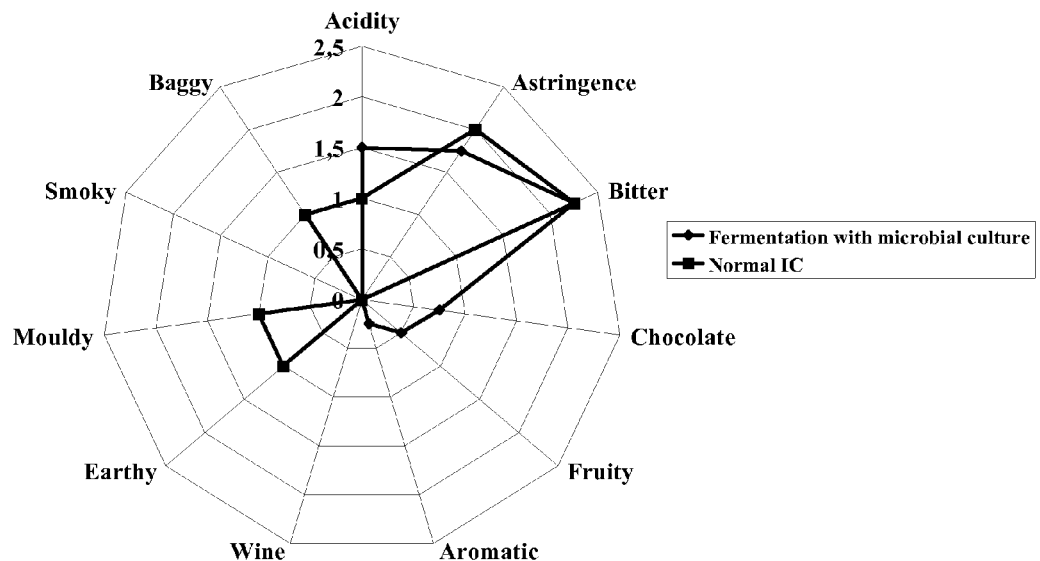
FIG. 1 shows the results of a taste panel experiment conducted on samples of cocoa beans that have been subjected to a natural fermentation process as compared to cocoa beans that have been fermented by using a microbial composition according to the invention.

The present invention is directed to microbial starter cultures and uses and methods for regulating the fermentation of cocoa plant material, including cocoa beans and/or cocoa pulp.

The present starter cultures and methods allow for controlling or manipulating the development of desirable characteristics of the fermented cocoa beans and the cocoa products prepared there from. By means of example and not limitation, the present starter cultures method may allow for controlling the index of fermentation of cocoa beans (cut test, colouration), appearance and sensorial properties of the fermented beans, e.g., sensorial properties, organic acids, sugar alcohols, polyphenol, theobromine, or caffeine content of roasted beans, organoleptic characteristics (taste, flavour, aroma, texture, colour, rheology, crystallisation behaviour, etc.), nutritional characteristics, technological properties, quality assets (aroma, taste, flavour, fatty acid composition, polyphenol content, theobromine content, caffeine content, etc.) of cocoa products, such as, particularly chocolate.

More in particular, the invention is directed to the use of starter cultures for regulating cocoa fermentation, wherein said starter cultures comprise a combination of specific strains of microorganisms.

The term "microbial composition" intends to refer to a composition of micro-organisms as defined herein, which are added to the organic material, in particular cocoa plant material, preferably at the start of the fermentation process thereof.

As used herein, the term "strain" refers in general to a closed population of organisms of the same species. Accordingly, the term "strain of lactic acid bacteria and/or acetic acid bacteria" generally refers to a strain of a species of lactic acid bacteria and/or acetic acid bacteria. More particularly, the term "strain" refers to members of a microbial species, wherein such members have different genotypes and/or phenotypes. Herein, the term "genotype" encompasses both the genomic and the recombinant DNA content of a microorganism. Herein, the term "phenotype" refers to observable physical characteristics dependent upon the genetic constitution of a microorganism. As one skilled in the art would recognize, microbial strains are thus composed of individual microbial cells having a common genotype and/or phenotype. Further, individual microbial cells may have specific characteristics (e.g., a specific rep-PCR pattern) which may identify them as belonging to their particular strain.

A microbial strain may comprise one or more isolates of a microorganism. As used herein, the term "isolate" refers to cultured microorganisms grown from a single colony taken from a primary isolation plate. An isolate is presumed to be derived from a single microorganism.

As used herein, the terms "microorganism" or "microbial" cover any generally unicellular organism, which can be propagated and manipulated in a laboratory. In the present invention, the terms preferably relate to bacteria and/or yeast and/or fungi. In the present invention, the term microorganism typically denotes a live microorganism, i.e., capable of propagation and/or having metabolic activity.

The term "organic material" as used herein refers to living organisms or their remains and in particular relates to plant material. The term "plant material" includes anything that is or was live vegetation, in particular plants and any parts thereof, the latter including but not restricted to leafs, flowers, roots, seeds, stems, fruits, pods, beans, berries, grains, pulp and the like.

In the present invention, the plant material is preferably derived from any species of the genera *Theobroma* or *Herrania* or inter- and intra-species crosses thereof, and more preferably from the species *Theobroma cacao* and *Theobroma grandiflorum*. The species *Theobroma cacao* as used herein comprises all varieties, particularly all commercially useful varieties, including but not limited to Criollo, Forastero, Trinitario, Arriba, and crosses and hybrids thereof. Cocoa beans derived from the fruit pods of *Theobroma cacao* are the principal raw material for chocolate production. The cocoa beans are embedded in a mucilaginous pulp inside the pods. After the pods are harvested, the cocoa beans (usually including at least a portion of the surrounding pulp) are recovered from the pods. Accordingly, the plant material used in the method of the invention may preferably comprise cocoa beans derived from the fruit pods of *Theobroma cacao*, and may further comprise the pulp derived from the said fruit pods. In an embodiment, the plant material may consist essentially of cocoa beans and the pulp derived from the fruit pods of *Theobroma cacao*.

It is noted that the terms "cocoa" and "cacao" as used herein are considered as synonyms.

As used herein, the term "fermentation" refers generally to any activity or process involving enzymatic decomposition (digestion) of organic materials by microorganisms. The term "fermentation" encompasses both anaerobic and aerobic processes, as well as processes involving a combination or succession of one or more anaerobic and/or aerobic stages. In the present invention, fermentation preferably involves the decomposition (digestion) of plant material as defined above.

The term "controlled fermentation" as used herein is therefore intended to refer to a fermentation process that is regulated by using a microbial composition as defined herein.

The term "conventional" or "spontaneous" or "natural" fermentation intends to refer to a natural fermentation process wherein no microbial composition or starter culture has been added. A "spontaneous" fermentation or "natural fermentation" as used herein is one that employs microorganisms naturally present in and/or unconsciously introduced into the fermented organic material at the start or during the fermentation. By means of example and not limitation, in spontaneous fermentation of cocoa beans and pulp, microorganisms may be introduced after the beans and the pulp are released from the pods from natural microbiota present, for example, on workers' hands, tools (knifes, shovels, unwashed baskets, etc.) and in places of previous fermentations. Accordingly, in the above methods an otherwise spontaneous fermentation may be regulated by addition of a microbial composition as defined herein. Hereby, the microbial presence in the materials is altered and the fermentation is thereby regulated (controlled or modulated).

In an alternative embodiment, the methods may relate to regulating fermentation which would not be initiated without said regulating. In a typical example, this may occur when natural (indigenous) microbiota are removed or suppressed from the organic material prior to adding a microbial composition as defined herein. By means of example and not limitation, the natural microbiota present in the cocoa fermentation may be largely removed by de-pulping the recovered beans by various methods of the art, e.g., as known from GB2241146.

In a preferred embodiment, the present invention relates to the fermentation of plant material comprising the beans derived from *Theobroma cacao* and/or plant material consisting essentially of the beans and pulp derived from *Theobroma cacao*. As described above, in cacao production after removal of the beans (and the surrounding pulp) from the pods, the beans and pulp are typically subjected to a spontaneous fermentation, which is important for the characteristics of the resulting cocoa, such as its aroma, flavour and colour. It is thus an object of the present invention to provide a method for regulating the fermentation of organic material, preferably plant material, even more preferably plant material comprising the beans derived from *Theobroma cacao* and/or plant material consisting essentially of the beans and pulp derived from *Theobroma cacao* (the latter two plant materials are collectively referred to herein as "cocoa beans and pulp").

The term "regulating" as used herein in relation to the fermentation of organic material encompasses but is not limited to initiating a fermentation process and/or initiating a particular stage of the fermentation process; accelerating a fermentation process and/or accelerating a particular stage of the fermentation process; initiating and/or accelerating the transition from one stage of a fermentation process to another stage of the fermentation process (e.g., the transition from mainly yeast-mediated fermentation to mainly LAB-mediated fermentation, or from the mainly LAB-mediated fermentation to mainly AAB-mediated fermentation during the fermentation process of cocoa beans and pulp); altering the conditions of the fermentation, such as, e.g., temperature or pH; altering the composition of the fermented material (e.g., altering the decomposition or production of particular substances present in the fermented material); altering the identity and/or quantity of microbial strains present in and/or carrying out the fermentation process; enhancing or suppressing the growth of particular microorganisms etc.

By regulating the above and other aspects of fermentation, the present invention allows for controlling or manipulating, by means of example and not limitation, the rate of fermentation, the extent of fermentation, rapidity and productivity of the fermentation, the quality and/or quantity of both desirable and undesirable substances present in the fermented material, and characteristics of the fermented material and/or products obtained by further processing of the fermented material.

In a particular embodiment, by using a microbial composition according to the present invention for the fermentation of cocoa material as defined herein can be significantly accelerated, for instance fermentation may be up to 1.3, 1.5, 1.8, 2, 2.5, or even 3 times faster compared to natural fermentation processes. In another embodiment, by use of a microbial composition according to the present invention fermentation of the cocoa plant material as defined herein can significantly influence one or more fermentation processes/stages and thus fermentation productivity, and increase productivity preferably with at least 5%, preferably with at least 10%, at least 15%, or even at least 20% compared to natural fermentation processes.

In a particular embodiment, the invention provides for the incubation of a microbial composition according to the invention with cocoa material as defined herein at ambient temperature, which may for instance vary between 20 and 40° C.

In yet another particular embodiment, the invention provides for the incubation of a microbial composition according to the invention with cocoa material as defined herein for less than 4 days, or less than 3 days, or less than 2 days, or less than 1 day (24 hours).

In another embodiment, a microbial composition according to the present invention for the fermentation of cocoa material as defined herein the composition of the fermented cocoa beans can be significantly modified.

In a preferred embodiment, by using a microbial composition according to the present invention for the fermentation of cocoa material as defined herein the amount of remaining polyphenols may be at least 2 times higher, and for instance 3, 5, 7, or 9 times higher compared to amounts thereof in beans issued from natural fermentation processes. In another preferred embodiment, by using a microbial composition according to the present invention for the fermentation of cocoa material as defined herein the amount of epicatechin in fermented cocoa beans may be at least 1.5 times higher, and for instance 2 times higher compared to amounts thereof in beans issued from natural fermentation processes.

In a preferred embodiment, by using a composition according to the present invention the amount and composition of organic acids in fermented cocoa beans can be altered. The amount of organic acid e.g. lactic acid may be 5%, preferably with at least 10%, at least 15%, or even at least 20% compared to conventional (uncontrolled) fermentation processes.

Microbial Compositions and Controlled Fermentation Methods

In one aspect, the invention relates to the use of a microbial composition for regulating fermentation of plant material essentially consisting of beans and/or pulp derived from fruit pods of the species *Theobroma cacao*, wherein said composition comprises at least three *Lactobacillus* species and at least one *Acetobacter* species and at least one yeast species.

In another aspect, the invention relates to a method for regulating fermentation of plant material essentially consisting of beans and/or pulp derived from fruit pods of the species *Theobroma cacao*, said method comprising adding to the plant material a microbial composition as defined herein.

Embodiments of microbial compositions for use in accordance with the present invention will now be described in more detail.

More in particular, the invention relates to the use of a microbial composition comprising:
  *Lactobacillus plantarum, Lactobacillus fermentum*, and *Acetobacter pasteurianus* and
  at least one additional *Lactobacillus* species selected from the group consisting of *Lactobacillus parafarraginis, Lactobacillus farraginis, Lactobacillus diolivorans, Lactobacillus faeni* and *Lactobacillus paracasei*, and
  at least one strain of a yeast species of a genus chosen from the group consisting of *Saccharomyces* and *Candida*.

Particularly a microbial composition as intended herein may comprise, consist essentially of or consist of:
  *Lactobacillus plantarum, Lactobacillus fermentum* and *Acetobacter pasteurianus* and
  at least one additional *Lactobacillus* species selected from the group consisting of *Lactobacillus parafarraginis, Lactobacillus farraginis, Lactobacillus diolivorans, Lactobacillus faeni* and *Lactobacillus paracasei*, preferably *Lactobacillus parafarraginis*, and
  at least one strain of a yeast species of a genus chosen from the group consisting of *Saccharomyces* and *Candida*, preferably *Saccharomyces*, more preferably wherein said yeast species is *Saccharomyces cerevisiae*.

More particularly a microbial composition as intended herein may comprise, consist essentially of or consist of:
  *Lactobacillus plantarum, Lactobacillus fermentum, Lactobacillus parafarraginis* and *Acetobacter pasteurianus* and
  at least one strain of a yeast species of a genus chosen from the group consisting of *Saccharomyces* and *Candida*, preferably *Saccharomyces*, more preferably wherein said yeast species is *Saccharomyces cerevisiae*.

In another embodiment the invention relates to the use of a microbial composition comprising:
  *Lactobacillus plantarum, Lactobacillus fermentum, Acetobacter pasteurianus, Lactobacillus parafarraginis*, and
  at least one additional *Lactobacillus* species selected from the group consisting of *Lactobacillus farraginis, Lactobacillus diolivorans, Lactobacillus faeni* and *Lactobacillus paracasei*, and
  at least one strain of a yeast species of a genus chosen from the group consisting of *Saccharomyces* and *Candida*.

In an embodiment a microbial composition as intended herein may comprise, consist essentially of or consist of:
  *Lactobacillus plantarum, Lactobacillus fermentum, Lactobacillus parafarraginis* and *Acetobacter pasteurianus* and
  at least one strain of a yeast species of a genus chosen from the group consisting of *Saccharomyces* and *Candida*, preferably *Saccharomyces*, more preferably wherein said yeast species is *Saccharomyces cerevisiae*, and
  optionally and preferably, at least one additional *Lactobacillus* species selected from the group consisting of *Lactobacillus farraginis, Lactobacillus diolivorans, Lactobacillus faeni* and *Lactobacillus paracasei*.

In yet another embodiment the invention relates to the use of a microbial composition comprising:
  *Lactobacillus plantarum, Lactobacillus fermentum, Acetobacter pasteurianus, Lactobacillus farraginis*, and
  at least one additional *Lactobacillus* species selected from the group consisting of *Lactobacillus parafarraginis, Lactobacillus diolivorans, Lactobacillus faeni* and *Lactobacillus paracasei*, and
  at least one strain of a yeast species of a genus chosen from the group consisting of *Saccharomyces* and *Candida*.

In an embodiment a microbial composition as intended herein may comprise, consist essentially of or consist of:
  *Lactobacillus plantarum, Lactobacillus fermentum, Acetobacter pasteurianus, Lactobacillus farraginis*, and
  at least one strain of a yeast species of a genus chosen from the group consisting of *Saccharomyces* and *Candida*, preferably *Saccharomyces*, more preferably wherein said yeast species is *Saccharomyces cerevisiae*, and
  optionally and preferably, at least one additional *Lactobacillus* species selected from the group consisting of *Lactobacillus parafarraginis, Lactobacillus diolivorans, Lactobacillus faeni* and *Lactobacillus paracasei*, preferably *Lactobacillus parafarraginis*.

In still another embodiment the invention relates to the use of a microbial composition comprising:
  *Lactobacillus plantarum, Lactobacillus fermentum, Acetobacter pasteurianus, Lactobacillus diolivorans*, and
  at least one additional *Lactobacillus* species selected from the group consisting of *Lactobacillus parafarraginis, Lactobacillus farraginis, Lactobacillus faeni* and *Lactobacillus paracasei*, and
  at least one strain of a yeast species of a genus chosen from the group consisting of *Saccharomyces* and *Candida*.

In an embodiment a microbial composition as intended herein may comprise, consist essentially of or consist of:
Lactobacillus plantarum, Lactobacillus fermentum, Acetobacter pasteurianus, Lactobacillus diolivorans, and
at least one strain of a yeast species of a genus chosen from the group consisting of *Saccharomyces* and *Candida*, preferably *Saccharomyces*, more preferably wherein said yeast species is *Saccharomyces cerevisiae*, and
optionally and preferably, at least one additional *Lactobacillus* species selected from the group consisting of *Lactobacillus parafarraginis*, *Lactobacillus farraginis*, *Lactobacillus faeni* and *Lactobacillus paracasei*, preferably *Lactobacillus parafarraginis*.

Another embodiment of a microbial composition for use in accordance with the present invention comprises a composition comprising:
Lactobacillus plantarum, Lactobacillus fermentum, Acetobacter pasteurianus, Lactobacillus faeni, and
at least one additional *Lactobacillus* species selected from the group consisting of *Lactobacillus parafarraginis*, *Lactobacillus farraginis*, *Lactobacillus diolivorans* and *Lactobacillus paracasei*, and
at least one strain of a yeast species of a genus chosen from the group consisting of *Saccharomyces* and *Candida*.

In an embodiment a microbial composition as intended herein may comprise, consist essentially of or consist of:
Lactobacillus plantarum, Lactobacillus fermentum, Acetobacter pasteurianus, Lactobacillus faeni, and
at least one strain of a yeast species of a genus chosen from the group consisting of *Saccharomyces* and *Candida*, preferably *Saccharomyces*, more preferably wherein said yeast species is *Saccharomyces cerevisiae*, and
optionally and preferably, at least one additional *Lactobacillus* species selected from the group consisting of *Lactobacillus parafarraginis*, *Lactobacillus farraginis*, *Lactobacillus diolivorans* and *Lactobacillus paracasei*, preferably *Lactobacillus parafarraginis*.

Yet another embodiment of a microbial composition for use in accordance with the present invention comprises a composition comprising:
Lactobacillus plantarum, Lactobacillus fermentum, Acetobacter pasteurianus, Lactobacillus paracasei, and
at least one additional *Lactobacillus* species selected from the group consisting of *Lactobacillus parafarraginis*, *Lactobacillus farraginis*, *Lactobacillus diolivorans* and *Lactobacillus faeni*, and
at least one strain of a yeast species of a genus chosen from the group consisting of *Saccharomyces* and *Candida*.

In an embodiment a microbial composition as intended herein may comprise, consist essentially of or consist of:
Lactobacillus plantarum, Lactobacillus fermentum, Acetobacter pasteurianus, Lactobacillus paracasei, and
at least one strain of a yeast species of a genus chosen from the group consisting of *Saccharomyces* and *Candida*, preferably *Saccharomyces*, more preferably wherein said yeast species is *Saccharomyces cerevisiae*, and
optionally and preferably, at least one additional *Lactobacillus* species selected from the group consisting of *Lactobacillus parafarraginis*, *Lactobacillus farraginis*, *Lactobacillus diolivorans* and *Lactobacillus faeni*, preferably *Lactobacillus parafarraginis*.

Still another embodiment of a microbial composition for use in accordance with the present invention comprises a composition comprising:
Lactobacillus plantarum, Lactobacillus fermentum, Acetobacter pasteurianus,
Lactobacillus parafarraginis, and Lactobacillus farraginis, and
at least one additional *Lactobacillus* species selected from the group consisting of *Lactobacillus diolivorans*, *Lactobacillus faeni* and *Lactobacillus paracasei*, and
at least one strain of a yeast species of a genus chosen from the group consisting of *Saccharomyces* and *Candida*.

In an embodiment a microbial composition as intended herein may comprise, consist essentially of or consist of:
Lactobacillus plantarum, Lactobacillus fermentum, Acetobacter pasteurianus, Lactobacillus parafarraginis, and Lactobacillus farraginis, and
at least one strain of a yeast species of a genus chosen from the group consisting of *Saccharomyces* and *Candida*, preferably *Saccharomyces*, more preferably wherein said yeast species is *Saccharomyces cerevisiae*, and
optionally and preferably, at least one additional *Lactobacillus* species selected from the group consisting of *Lactobacillus diolivorans*, *Lactobacillus faeni* and *Lactobacillus paracasei*.

Another example of a microbial composition for use in accordance with the present invention includes a composition comprising:
Lactobacillus plantarum, Lactobacillus fermentum, Acetobacter pasteurianus, Lactobacillus parafarraginis, and Lactobacillus diolivorans, and
at least one additional *Lactobacillus* species selected from the group consisting of *Lactobacillus farraginis*, *Lactobacillus faeni* and *Lactobacillus paracasei*, and
at least one strain of a yeast species of a genus chosen from the group consisting of *Saccharomyces* and *Candida*.

In an embodiment a microbial composition as intended herein may comprise, consist essentially of or consist of:
Lactobacillus plantarum, Lactobacillus fermentum, Acetobacter pasteurianus,
Lactobacillus parafarraginis, and Lactobacillus diolivorans, and
at least one strain of a yeast species of a genus chosen from the group consisting of *Saccharomyces* and *Candida*, preferably *Saccharomyces*, more preferably wherein said yeast species is *Saccharomyces cerevisiae*, and
optionally and preferably, at least one additional *Lactobacillus* species selected from the group consisting of *Lactobacillus farraginis*, *Lactobacillus faeni* and *Lactobacillus paracasei*.

Other bacteria that may be added to microbial compositions according to the invention include but are not limited to *Lactobacillus buchneri*, *Lactobacillus fabifermentans*, *Lactobacillus cacaonum*, and *Lactobacillus hilgardii*.

As indicated above, the invention relates to the use of a microbial composition as defined herein. The present microbial composition comprises at least one yeast strain. As used herein, the term "yeast" refers to a group of single-celled fungi, most of which are in the class Ascomycetes, and others in the class Basidiomycetes.

In an embodiment, the at least one strain of yeast belongs to a species of a genus chosen from the group consisting of *Saccharomyces* and *Candida*.

In a preferred embodiment, the at least one strain of yeast belongs to a species chosen from the group comprising or consisting of *Candida bombi, Candida pefficulosa, Candida rugopefficulosa, Candida rugosa, Candida intermedia, Candida krusei, Candida parapsilosis, Candida quercitrusa, Candida silvicola, Candida steffimalicola, Candida boidinii, Candida cacoai, Candida guiffiermondii, Candida reukaufii, Candida amapae, Candida diddensiae, Candida friedrichii, Candida humicola, Candida mycoderma, Candida neodendra, Candida tammaniensis, Candida tropicalis, Candida valida, Candida zemplinina, Saccharomyces cerevisiae*, and *Saccharomyces cerevisiae* var. *chevalieri*, and preferably *Candida bombi, Candida pefficulosa, Candida rugosa, Candida intermedia, Candida krusei, Candida cacoai, Candida guiffiermondii*, and *Saccharomyces cerevisiae*, and more preferably *Saccharomyces cerevisiae*.

In another embodiment, the present microbial composition further comprises at least one other yeast strain, different from a species of a genus chosen from the group consisting of *Saccharomyces* and *Candida* as indicated above. For example, in an embodiment, such at least one other strain of yeast may belong to a species of a genus chosen from the group comprising or consisting of *Brettanomyces, Cryptococcus, Debaryomyces, Geotrichum, Hanseniaspora, Hansenula, Issatchenkia, Kloeckera, Kluyveromyces, Lodderomyces, Pichia, Rhodotorula, Saccharomycopsis, Schizosaccharomyces, Scytaladium, Torulaspora, Torulopsis* or *Trichosporon*, and preferably *Cryptococcus, Hanseniaspora, Hansenula, Kluyveromyces*, or *Pichia*, and more preferably *Hanseniaspora, Kluyveromyces*, or *Pichia*. Further examples of yeast genera may include but are not limited to *Arxiozyma, Citeromyces, Dekkera, Holleya, Kodameae, Saturnispora, Starmera, Tetrapisispora, Williopsis* or *Zygosaccharomyces*.

In another embodiment, the present microbial composition consists essentially of *L. fermentum, L. plantarum, L. parafarraginis, L. farraginis, L. diolivorans, L. faeni, L. paracasei, L. casei, L. hilgardii, L. buchneri, Acetobacter pasteurianus, Saccharomyces cerevisiae*.

In another embodiment, the present microbial composition consists essentially of *L. fermentum, L. plantarum, L. parafarraginis, L. casei, L. buchneri, Acetobacter pasteurianus*, and *Saccharomyces cerevisiae* (Microbial composition A). In another embodiment, the present microbial composition consists essentially of *L. fermentum, L. plantarum, L. farraginis, L. hilgardii, Acetobacter pasteurianus* and *Saccharomyces cerevisiae* (Microbial composition B). In another embodiment, the present microbial composition consists essentially of *L. fermentum, L. plantarum, L. diolivorans, L. hilgardii, Acetobacter pasteurianus* and *Saccharomyces cerevisiae* (Microbial composition C). In another embodiment, the present microbial composition consists essentially of *L. fermentum, L. plantarum, L. faeni, L. casei, L. buchneri, Acetobacter pasteurianus* and *Saccharomyces cerevisiae* (Microbial composition D). In another embodiment, the present microbial composition consists essentially of *L. fermentum, L. plantarum, L. paracasei, L. casei, Acetobacter pasteurianus* and *Saccharomyces cerevisiae* (Microbial composition E). In another embodiment, the present microbial composition consists essentially of *L. fermentum, L. plantarum, L. parafarraginis, L. farraginis, L. hilgardii, Acetobacter pasteurianus* and *Saccharomyces cerevisiae* (Microbial composition F). In another embodiment, the present microbial composition consists essentially of *L. fermentum, L. plantarum, L. farraginis, L. diolivorans, L. casei, L. hilgardii, L. buchneri, Acetobacter pasteurianus* and *Saccharomyces cerevisiae* (Microbial composition G). In another embodiment, the present microbial composition consists essentially of *L. fermentum, L. plantarum, L. diolivorans, L. faeni, Acetobacter pasteurianus* and *Saccharomyces cerevisiae* (Microbial composition H). In another embodiment, the present microbial composition consists essentially of *L. fermentum, L. plantarum, L. faeni, L. paracasei, L. hilgardii, Acetobacter pasteurianus* and *Saccharomyces cerevisiae* (Microbial composition I). In another embodiment, the present microbial composition consists essentially of *L. fermentum, L. plantarum, L. parafarraginis, L. diolivorans, L. casei, L. hilgardii, L. buchneri, Acetobacter pasteurianus* and *Saccharomyces cerevisiae* (Microbial composition J). In another embodiment, the present microbial composition consists essentially of *L. fermentum, L. plantarum, L. farraginis, L. faeni, L. casei, Acetobacter pasteurianus* and *Saccharomyces cerevisiae* (Microbial composition K). In another embodiment, the present microbial composition consists essentially of *L. fermentum, L. plantarum, L. diolivorans, L. paracasei, L. hilgardii, Acetobacter pasteurianus*, and *Saccharomyces cerevisiae* (Microbial composition L). In another embodiment, the present microbial composition consists essentially of *L. fermentum, L. plantarum, L. parafarraginis, L. diolivorans, L. paracasei, L. buchneri, Acetobacter pasteurianus, Saccharomyces cerevisiae* (Microbial composition M). In another embodiment, the present microbial composition consists essentially of *L. fermentum, L. plantarum, L. parafarraginis, L. farraginis, L. diolivorans, L. faeni, L. paracasei, L. casei, L. hilgardii, L. buchneri, Acetobacter pasteurianus* and *Saccharomyces cerevisiae* (Microbial composition N). In another embodiment, the present microbial composition consists essentially of *L. fermentum, L. plantarum, L. parafarraginis, Acetobacter pasteurianus* and *Saccharomyces cerevisiae* (Microbial composition O).

Table 1 provides further non-limitative examples of microbial compositions which are suitable for use in the present invention.

TABLE 1

| Microbial Composition | L. fermentum | L. plantarum | L. parafarraginis | L. farraginis | L. diolivorans | L. faeni | L. paracasei |
|---|---|---|---|---|---|---|---|
| A | + | + | + | | | | |
| B | + | + | | + | | | |
| C | + | + | | | + | | |
| D | + | + | | | | + | |
| E | + | + | | | | | + |
| F | + | + | | + | + | | |
| G | + | + | | | + | + | |
| H | + | + | | | | + | + |
| I | + | + | | | | + | + |

TABLE 1-continued

| | | | | | | | |
|---|---|---|---|---|---|---|---|
| J | + | + | + | | + | | |
| K | + | + | | + | | + | |
| L | + | + | | | + | | + |
| M | + | + | + | | + | | + |
| N | + | + | + | + | + | + | + |
| O | + | + | + | | | | |

| Microbial Composition | L. casei | L. hilgardii | L. buchneri | Acetobacter pasteurianus | Saccharomyces cerevisiae |
|---|---|---|---|---|---|
| A | + | | + | + | + |
| B | | + | | + | + |
| C | | + | | + | + |
| D | + | | + | + | + |
| E | + | | | + | + |
| F | | + | | + | + |
| G | + | + | + | + | + |
| H | | | | + | + |
| I | | + | | + | + |
| J | + | + | + | + | + |
| K | + | | | + | + |
| L | | + | | + | + |
| M | | | + | + | + |
| N | + | + | + | + | + |
| O | | | | + | + |

In another embodiment of the present invention, the fermentation of the plant material comprising beans derived from *Theobroma cacao* and/or plant material consisting, preferably essentially, of the beans and pulp derived from *Theobroma cacao* (collectively "cocoa beans and pulp") may be carried out in heaps, boxes (e.g., wooden or steel boxes), baskets, trays, and other means, such as generally used in the art. In a preferred embodiment, the said fermentation may be carried out in heaps or boxes.

In another embodiment, the invention relates to the use of a microbial composition as defined above at early stages of a fermentation process, during the first 1, 2, 3, 4, 5, 7, 10, 12, 15, 18, 20, 22 or 24 hours of the fermentation. In an another embodiment, the invention therefore provides a method for regulating fermentation of organic material, more particularly plant material, even more particularly cocoa beans and pulp, comprises adding thereto a composition as defined above at the start and/or earlier stages of the fermentation, e.g., at the start and/or during the first 24 hours of the fermentation, and for instance during the first 1, 2, 3, 4, 5, 7, 10, 12, 15, 18, 20 or 22 hours of the fermentation, a composition as defined herein.

In an embodiment, microbial compositions of the invention may be a starter culture. The term "culture" refers to any sample or specimen which is known to contain or suspected of containing one or more microorganisms. The term as used herein also encompasses starter culture and co-culture. The term "starter culture" refers to a composition comprising live microorganisms that are capable of initiating or effecting fermentation of organic material, optionally after being cultivated in a separate starter medium for obtaining a high density culture. Accordingly, in an embodiment, microbial compositions of the invention may be a high density culture obtained by propagating a starter culture in a suitable medium.

A starter culture may be, e.g., a liquid culture, liquid pressed culture, frozen or dried form, including, e.g., freeze dried form and spray/fluid bed dried form, or frozen or freeze-dried concentrated. The culture may be packed in vacuum, or under an atmosphere of, e.g., $N_2$, $CO_2$ and the like. For example, a starter culture may be produced and distributed in sealed enclosures, preferably non-pyrogenic, which can be made of a rigid, non-flexible or flexible suitable plastic or other material, to the fermentation place and may be either added to organic material to be fermented, or optionally first cultivated in a separate starter medium to obtain a high density culture.

A starter culture may also contain, in addition to the microorganisms, buffering agents and growth stimulating nutrients (e.g., an assimilable carbohydrate or a nitrogen source), or preservatives (e.g., cryoprotective compounds) or other carriers, if desired, such as milk powder or sugars.

It may be preferred that a starter culture or a high density culture contains at least $10^2$ colony forming units (CFU) of bacterial strains and optionally of one or more yeast strains of the invention, such as at least $10^3$ CFU/g, at least $10^4$ CFU/g, e.g., at least $10^5$ CFU/g, at least $10^6$ CFU/g, e.g., at least $10^7$ CFU/g, at least $10^8$ CFU/g, e.g., at least $10^9$ CFU/g, at least $10^{10}$ CFU/g, e.g., at least $10^{11}$ CFU/g, at least $10^{12}$ CFU/g, or at least $10^{13}$ CFU/g.

In an embodiment, a microbial composition as defined above may be a starter culture or a high density culture, comprising at least $10^2$ CFU (colony forming units) of bacterial strains per g plant material, and for instance at least $10^3$ CFU/g, at least $10^4$ CFU/g, e.g., at least $10^5$ CFU/g, at least $10^6$ CFU/g, e.g., at least $10^7$ CFU/g, at least $10^8$ CFU/g, e.g., at least $10^9$ CFU/g, at least $10^{10}$ CFU/g, e.g., at least $10^{11}$ CFU/g, at least $10^{12}$ CFU/g, or at least $10^{13}$ CFU/g of the organic material.

Without limitation, a preferred microbial composition as taught herein may comprise, consist essentially of or consist of:

between $10^3$ and $10^7$ CFU/g of the plant material, preferably between $10^4$ and $10^6$, more preferably between $10^4$ and $10^5$, such as very preferably between $5 \times 10^4$ and $5 \times 10^5$ CFU/g of the plant material *Lactobacillus plantarum*;

between $10^3$ and $10^7$ CFU/g of the plant material, preferably between $10^4$ and $10^6$, more preferably between $10^4$ and $10^5$, such as very preferably between $5 \times 10^4$ and $5 \times 10^5$ CFU/g of the plant material *Lactobacillus fermentum*;

between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material *Acetobacter pasteurianus*;

between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material of at least one additional *Lactobacillus* species selected from the group consisting of *Lactobacillus parafarraginis*, *Lactobacillus farraginis*, *Lactobacillus diolivorans*, *Lactobacillus faeni* and *Lactobacillus paracasei*, preferably *Lactobacillus parafarraginis*, and between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material of at least one strain of a yeast species of a genus chosen from the group consisting of *Saccharomyces* and *Candida*, preferably *Saccharomyces*, more preferably wherein said yeast species is *Saccharomyces cerevisiae*.

Further disclosed is use of a microbial composition for regulating fermentation of plant material essentially consisting of beans and/or pulp derived from fruit pods of the species *Theobroma cacao*, wherein said composition comprises, consists essentially of or consists of:

between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material *Lactobacillus plantarum*;

between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material *Lactobacillus fermentum*;

between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material *Acetobacter pasteurianus*; and between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material of at least one strain of a yeast species of a genus chosen from the group consisting of *Saccharomyces* and *Candida*, preferably *Saccharomyces*, more preferably wherein said yeast species is *Saccharomyces cerevisiae*.

Further disclosed is use of a microbial composition for regulating fermentation of plant material essentially consisting of beans and/or pulp derived from fruit pods of the species *Theobroma cacao*, wherein said composition comprises, consists essentially of or consists of:

between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material *Lactobacillus plantarum*;

between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material *Lactobacillus fermentum*; and between $10^3$ and $10^7$ CFU/g of the plant material, preferably between $10^4$ and $10^6$, more preferably between $10^4$ and $10^5$, such as very preferably between $5\times10^4$ and $5\times10^5$ CFU/g of the plant material *Acetobacter pasteurianus*.

In accordance with the present invention, use of any of the compositions as defined herein during fermentation of cocoa beans has effects on the physical properties (e.g. appearance including colour), organoleptic properties (e.g. flavour) and (bio)chemical composition of the fermented cocoa beans.

In one embodiment, use of the present compositions enable to obtain a higher number of fermented cocoa beans which have good qualitative properties compared to natural fermentation processes, e.g. up to 10% and preferably up to 20% more fermented cocoa beans which have good qualitative properties, e.g. which are not infected and/or broken, and have a satisfying colour and appearance. Qualitative properties of beans can be evaluated using standard methods such as appearance and cut tests (see example section below).

In another embodiment, use of the present compositions enable to obtain fermented cocoa beans having optimal levels of (bio)chemical components such as but not limited to organic molecules, including lactic acid, acetic acid, citric acid, alcohols including ethanol, sugar alcohols including mannitol and erythritol, esters, polyphenols, including epicatechin, alkaloids (theobromine, caffeine) etc. . . . or lower or no levels of mycotoxins.

Fermented Plant Material

In another aspect, the invention also relates to cocoa beans obtained or obtainable by carrying out the methods of the present invention and to uses thereof, e.g. for preparing cocoa products and/or for preparing food products. Cocoa beans obtained or obtainable according to the present methods are surprisingly easy to process, for example the beans can easily be dried.

The invention provides fermented cocoa beans having one or more of the following features.

Cocoa beans according to the invention are high-flavoured cocoa products and have reproducible quality, flavour and/or organoleptic properties. Further, cocoa beans obtained or obtainable according to the present method retain their flavour and organoleptic properties for a prolonged time.

In another embodiment, the present compositions enable to obtain fermented beans having elevated amounts of polyphenols. In another preferred embodiment, the invention relates to fermented cocoa beans having a total amount of polyphenols which is at least 1.5 times, and for instance at least 2 times higher than the amounts measured in beans that have been subjected to a natural fermentation process.

In another preferred embodiment the invention relates to fermented cocoa beans having an amount of epicatechin which is at least 2 times, and for instance at least 3, 5 or 7 times higher than the amounts measured in beans that have been subjected to a natural fermentation process. For instance fermented cocoa beans are provided in accordance with the present invention having an amount of epicatechin which is higher than 1000 ppm, and preferably higher than 2000 ppm.

In an embodiment, the invention relates to cocoa beans that have an amount of free amino acids (FAA) selected from the group comprising or consisting of alanine, phenylalanine, tryptophan, leucine, and valine, and preferably selected from the group comprising or consisting of alanine, phenylalanine and tryptophan, which is at least 10% lower than in cocoa beans that have been subjected to a spontaneous fermentation process. The term "free" in this context refers to amino acids that are not covalently bound to another moiety.

In another embodiment, use of the present microbial composition for fermenting cocoa beans has the effect of inducing particular colour changes in the beans.

In particular, in an embodiment, the invention provides cocoa beans (and powders or liquor) that are particularly light. A number of objective methods for measuring the colour of powders, such as cocoa powder or liquor, are known. In one method, the Hunter colour system or CIE 1976 (CIELAB) and like systems, colour may be described in terms of coordinates L, "a*" and "b*". The L coordinate is consistent with the Value of Lightness, and from the a* and b* coordinates, the Chroma and Hue can be calculated. The lower the L-value, the darker the cocoa powder will appear; Chroma (C)—the intensity of a colour by which one distinguishes a bright or gray colour, where the higher the C-value, the brighter the powder will be; and Hue (H)— referring to colour in daily speech, such as red, yellow, or blue.

More in detail, the Hunter colour system is a well-known means of defining the colour of a given material. A complete technical description of the system can be found in an article by Hunter, "Photoelectric Color Difference Meter," Journal of the Optical Society of America, 1958, vol. 48, 985-95. By means of a further explanation, the Hunter colour system can be described in terms of a three-dimensional colour solid. This solid contains all possible colours and has three perpendicular axes passing through its geometric centre. The location of any point within the figure can be determined by reference to its coordinates on the three axes. Therefore, any colour can be defined in terms of the three coordinates. In the Hunter colour system the "L" scale contains 100 equal units of division. Absolute black is at the bottom of the scale (L=0) and absolute white is at the top of the scale (L=100). Thus, in measuring Hunter colour values the lower the "L" scale value the darker the colour. In the Hunter colour system the "a*" scale measures colour hue and chroma between red and green. The "b*" scale measures colour hue and chroma between blue and yellow. Hue is analogous to the dominant wavelength, while chroma relates to the colour purity. Hence, the use of the Hunter colour system provides an accurate and reproducible means of colour measurement. Techniques have been developed which permits the use of this colour measurement system on materials of practically all shapes, sizes and compositions. Devices specifically designed for the measurement of colour on the Hunter colour scales are described inter alia in U.S. Pat. No. 3,003,388.

Cocoa powders or cocoa liquor prepared from beans fermented according to the invention preferably have a L colour co-ordinate value which is higher than 14, e.g., higher than 15, preferably higher than 16, e.g., higher than 17, more preferably higher than 18, and for instance and very preferably higher than 19, or 20 or higher, such as for example L colour co-ordinate value between 14 and 20, preferably between 16 and 20, more preferably between 17 and 20 or between 18 and 20 such as between 18 and 19. Surprisingly, this lighter colour is not observed with conventionally fermented beans or with beans that have been fermented using a prior art microbial composition (see also examples 1 and 5).

According to the present invention, the colour of the cocoa-beans or of cocoa products derived there from can be measured as follows. The cocoa-beans or cocoa-products are preferably defatted to yield less than 5 wt % of fat followed by washing and centrifugation. In preferred embodiment a powder or liquor is formed of the product. After drying for instance at room temperature, a sample is placed in a petri-dish and measured through the bottom of the dish using a colorimeter with the well-known Hunter L*, a*, b* scale. The suitable colorimeter is for instance a Minolta CM-2002 spectrophotometer. The conditions for colour measurement can be as follows: CIELAB III: D65, Obs: 10°, 3 flashes, mode: SCE and external colour at 20° C.

Unexpectedly, the beans that were fermented using a microbial composition according to the invention showed a light-breaking effect. The beans fermented using a microbial composition as provided herein had a lighter colour than conventionally fermented beans, and in particular are light brown. The colour of the beans fermented in accordance with the present invention is therefore less influenced by the natural brown cocoa colour. The colour of the beans fermented in accordance with the present invention is in fact comparable with the colour of Java beans, which are known to have a light colour. The present invention thus permits to provide beans of a non-Java origin that when fermented have a colour comparable to the colour of Java beans (see for instance example 5).

A particular advantage of the light-coloured fermented cocoa beans obtained in accordance with the present invention, is that such beans can be used to make dark chocolate, i.e. chocolate having a relatively high amount of cocoa solids, but showing a lighter colour than conventionally dark chocolate (see further below).

Downstream Processing of Cocoa Beans Fermented According to the Invention

In an embodiment, fermented cocoa beans obtained with the herein described controlled fermentation method can undergo further treatments, either before and/or after adding a microbial composition as defined herein.

The invention provides in another aspect a method for processing the cocoa beans that have been fermented according to the present invention into cocoa products, and the downstream cocoa products or cocoa-derived material thereby obtained. The terms "cocoa products" and "cocoa-derived materials" are used herein as synonyms and refer to products that are prepared using cocoa beans. The products or materials intend to refer to the materials prepared starting from cocoa beans that have been subjected to a controlled fermentation as described herein. Cocoa products can be in a liquid form or in a dry or lyophilized form, such as in the form of granules, pellets, or a powder.

In a preferred embodiment said "cocoa products" or "cocoa-derived materials" include cocoa nibs, cocoa flakes, cocoa cake, cocoa powder, cocoa liquor and chocolate, including dark chocolate, milk chocolate or white chocolate. These terms are all well-known to a person skilled in the art but are therefore only briefly explained hereafter.

The term "cocoa nib" refers to the cocoa bean without the shell.

The term "cocoa liquor" refers to ground cocoa nibs. Cocoa liquor is prepared by grinding cocoa nibs into a dark paste known. On cooling, cocoa liquor yields cocoa mass. When the nibs are ground up into a coarse uniform paste, they form what is known as "cocoa flakes." The term "cocoa flakes" thus refers to cocoa liquor in the form of solid flakes.

Cocoa liquor can be processed into two different components: cocoa powder and cocoa butter. The cocoa liquor is pressed into cocoa cake by removing most of the cocoa butter. The term "cocoa cake" refers to the cocoa solids or cocoa mass remaining after extraction of fat (cocoa butter)

by pressing. Cocoa cakes can be broken up and ground into a fine cocoa powder. "Cocoa powder" refers to cocoa solids.

"Cocoa butter" is the fat component of chocolate liquor, whereas the remaining part of the chocolate liquor is cocoa solids or cocoa mass. For instance, to produce dark chocolate, cocoa nibs or cocoa mass are mixed with sugar and sufficient cocoa butter to enable the chocolate to be molded. To produce milk chocolate, cocoa mass and cocoa butter are mixed with sugar and milk powder, while for white chocolate cocoa butter (no cocoa mass) is mixed with sugar and milk powder.

In another aspect, the present invention encompasses a method for producing red or purple cocoa products. To that end, the invention provides a method wherein cocoa products derived from cocoa beans that have been fermented with a microbial composition as defined herein are further treated with an acid or an aqueous acidic solution.

The Applicants have unexpectedly shown that controlled fermentation of cocoa beans using a microbial composition as defined herein and the subsequent acid-treatment of cocoa-derived materials prepared from these fermented beans results in coloured cocoa-derived materials, such as coloured cocoa nibs, cocoa flakes, cocoa cake, cocoa liquor, cocoa powder or chocolate products. More particularly, the Applicants have shown that controlled fermentation of cocoa beans using a microbial composition as defined herein and the subsequent acid-treatment of cocoa-derived materials prepared from these fermented beans results in red or purple cocoa-derived materials as given above. Moreover, if the acidic conditions used to produce the red or purple cocoa-derived materials are controlled, in particular if for instance the pH, water content, temperature and length of reaction are controlled, then the level of polyphenols present in the products can be preserved, and red or purple coloured cocoa-derived materials can be produced.

The Applicants have shown that at the end of the fermentation process as described herein, cocoa beans were lighter and show a light-breaking effect. Nevertheless, it was further shown that acid treatment of cocoa-materials (such as cocoa nibs or cocoa liquor) obtained from these fermented beans resulted in red/purple materials. Surprisingly, despite the fact that the fermented cocoa beans did not have a dark brown colour, they could be processed into downstream cocoa-materials showing an excellent red/purple colour when applying an acid-treatment step as defined herein.

Another unexpected effect is that the use of cocoa materials derived from fermented beans as defined herein, permitted to reduce or even substantially mask the acid taste that is obtained as a result of the acid-treatment of the cocoa materials. By using well-fermented beans as starting material to produce red or purple cocoa products, surprisingly products of an excellent quality can be obtained that do not have the drawback of tasting (too) acid.

Another important beneficial effect of using beans that have been fermented according to the invention for producing red or purple cocoa products, is that standardized starting material, i.e. well-fermented beans of a reproducible quality and composition, can be used to prepare red or purple cocoa products.

In a particular embodiment, the present invention thus provides red or purple cocoa-derived materials selected from the group comprising or consisting of cocoa nibs, cocoa flakes, cocoa liquor, cocoa cake, cocoa powder, or food products such as chocolate products prepared with one or more of these cocoa products.

In an embodiment, the invention provides a process for producing a red or purple cocoa-derived material, comprising the steps of:
  a) providing cocoa beans that have been fermented with a microbial composition as defined herein,
  b) preparing a cocoa-derived material from the fermented cocoa beans of step a), and
  c) treating the cocoa-derived material of step b) with an acid or with an aqueous acidic solution.

The cocoa-derived material may be selected from the group comprising or consisting of cocoa nibs, cocoa flakes, cocoa cake, cocoa powder, cocoa liquor and chocolate. In a preferred embodiment said cocoa-derived material refers to cocoa nibs or cocoa liquor.

It shall be clear that where cocoa nibs, cocoa flakes, cocoa cake, cocoa powder, cocoa liquor and chocolate are prepared in step b) of the above method, additional steps other than those given in the above method will be involved in order to obtain the specific product. Techniques to be applied for preparing products derived from cocoa beans are well known in the art and will not be elaborated into detail herein. Nevertheless, by way of example, a few embodiments are provided hereunder.

In an embodiment, the cocoa-derived material is cocoa nibs and the above method further comprises the step of deshelling the fermented cocoa beans.

In another embodiment, the cocoa-derived material is cocoa flakes and the above method further comprises the step of breaking the nibs to form flakes.

In another embodiment of the process, the cocoa-derived material is cocoa liquor and the above method further comprises the step of grinding the nibs to form a cocoa liquor.

In yet another embodiment, the cocoa-derived material is a red or purple chocolate product and the above method further comprises the steps of: (i) grinding the nibs to form a cocoa liquor; and (ii) combining the cocoa liquor with cocoa butter or a replacement fat to form a red or purple chocolate product. Additionally the method for producing red or purple chocolate may further comprise the steps of conching, tempering and molding.

Hereunder, it will first be elaborated how the acid-treatment is carried out on cocoa nibs derived from fermented cocoa beans that have been fermented with the herein disclosed fermentation method. Thereafter, acid-treatment of cocoa-derived materials such as cocoa liquor will be described.

In an embodiment, the invention relates to a method for producing red or purple cocoa nibs, comprising the steps of:
  a) providing cocoa beans that have been fermented with a microbial composition as defined herein,
  b) preparing cocoa nibs from the fermented beans of step a),
  c) treating the cocoa nibs of step b) with an acid or with an aqueous acidic solution.

The cocoa nibs obtained in step c) my optionally be washed and/or dried before being further processed. Techniques that can be used for preparing cocoa nibs from cocoa beans are well known from in the art and are therefore not elaborated into detail herein.

In an embodiment, the cocoa nibs used in the above method are not roasted or treated with alkali prior to acid treatment. The cocoa nibs used to obtain red or purple cocoa nibs are fermented as defined herein, and can optionally be washed with water, dried (e.g. in the sun) and/or can undergo size reduction, prior to treatment with an acid as explained herein. In a particularly preferred embodiment, the method does not comprise any step of alkalization or roasting either before and/or after acid treatment as described herein.

Treatment of the cocoa nibs with an aqueous acidic solution encompasses the step of bringing an acid or an aqueous acidic solution into contact with the said cocoa nibs. This can be done by means of any method, e.g. by soaking, immersing, or washing the cocoa nibs with the aqueous acidic solution, and/or by spraying an aqueous acidic solution onto said nibs.

Optionally, the cocoa nibs may be dried before they are brought into contact with an aqueous acidic solution as provided herein. Drying of cocoa nibs can be done by means of conventional drying techniques such as e.g. sun, microwave hot air, commonly known in the art. Preferably, in such case the cocoa nibs are dried until a moisture content of the mixture of less than 10%, especially until a moisture content of 9, 8, 7, 6, or 5%, is reached.

The acid that can be used to treat cocoa nibs according to the invention may be a mineral acid, for example selected from the group comprising or consisting of hydrochloric acid, phosphoric acid and sulphuric acid. In another embodiment, the acid that can be used to treat cocoa nibs according to the invention may be an organic acid, for example selected from the group comprising or consisting of citric acid, lactic acid, tartaric acid, ascorbic acid and acetic acid. In a preferred embodiment of the invention, the acid is a food-grade acceptable acid. When selecting the acids, it should be borne in mind that they should not impair the flavour of the cocoa beans but readily penetrate into the cocoa beans. In a preferred embodiment of the invention, the acid is phosphoric acid, lactic acid, citric acid, ascorbic acid or acetic acid, and preferably phosphoric acid.

In one embodiment, the acid may be added to the cocoa nibs in the form of a solid, such as, for example, a powder. In an example, the acid could be added as a powder of citric acid or tartaric acid.

In another embodiment, the acid may be added to the cocoa nibs in the form of an aqueous acidic solution, i.e. obtained by combining the acid with water. Preferably, the aqueous acidic solution is a solution having a pH lower than 6, preferably lower than 5, and preferably lower than 4, and for instance has a pH of between 1 and 4 or between 2 and 3.

The acid or acidic solution may preferably comprise from 0.5 wt % to 20 wt % acid, more preferably from 1 to 10 wt % acid, most preferably from 2 to 5 wt % acid based on the weight of the solution.

The cocoa nibs can be treated with the acid/acidic solution under agitation, for example by using a magnetic stirrer or a rod.

The acid-treatment of the cocoa nibs should be sufficiently long to bring about sufficient acid penetration of the material. In another embodiment the method therefore comprises treating the cocoa nibs within the acid or an aqueous acidic solution for a time period of up to 24 hours, and for instance of up to 12 hours. In an example, the cocoa nibs may be treated with the acid or the aqueous acidic solution for a period of from about 2 to 8 hours, preferably from about 3 to 6 hours. In a particularly preferred example, the cocoa nibs may be treated with the acid or the aqueous acidic solution for a period of from about 4 to 5 hours. In another example the soaking time may, however, also be a few minutes, for example at least 5 minutes. In another preferred embodiment the contact and reaction period is from 20 to 60 minutes.

In another embodiment, the temperature during acid treatment is lower than 50° C., and preferably is comprised between 5 and 30° C.

In a particularly preferred embodiment, the cocoa nibs are treated with an acidic aqueous solution, preferably having a pH comprised between 1 and 3, for a period comprised between 3 and 6 hours and at a temperature comprised between 5 and 30° C.

It has been unexpectedly found that controlling the reaction conditions in this way produces coloured (red/purple) cocoa nibs and permits to substantially preserve the level of polyphenols present in the cocoa nibs. The obtained cocoa nibs can than be further processed as explained above. The colours in the cocoa nibs are hereby substantially maintained, such that when the nibs are for instance further processed into cocoa flakes, cocoa cake, cocoa powder, cocoa liquor and/or chocolate, the obtained red/purple cocoa nibs may yield red/purple cocoa flakes, red/purple cocoa cake, red/purple cocoa powder, red/purple cocoa liquor and/or red/purple chocolate.

In another embodiment, the invention provides a method for producing a red or purple cocoa liquor comprising the steps of:
  a) providing cocoa beans that have been fermented with a microbial composition as defined herein,
  b) preparing a cocoa liquor from the fermented cocoa beans of step a), and
  c) treating the cocoa liquor of step b) or a composition comprising the cocoa-liquor of step
  b) with an acid or with an aqueous acidic solution.

In an example, cocoa liquor derived from cocoa beans that have been fermented with a microbial composition as provided herein, and which have not previously been treated with an acid may be treated with an acid or acid solution as described herein. Preferably red or purple cocoa liquor is thereby produced. The cocoa liquor that has been treated with said acid can then be used in the production of chocolate, in particular red or purple chocolate.

The cocoa liquor can be directly treated with an acid or aqueous acidic solution. Alternatively, a composition comprising a cocoa liquor such as chocolate liquor, chocolate or a chocolate-like product, may be treated with acid. In a preferred embodiment, composition comprising the cocoa liquor is treated with acid after the step of refining, and preferably before, during or after the process of conching.

The treatment with acid may be as defined in any of the embodiments given above for the cocoa nibs. When applying the acid treatment on cocoa liquor, similar conditions of for instance acid concentration, pH conditions, types of acids, periods of treatment, temperatures, etc. are applied as described above for the cocoa nibs.

The cocoa beans fermented according to the present method, or cocoa-materials derived there from, may further undergo additional treatment(s), beside the above-described acid treatment. For instance, in an embodiment, the cocoa beans may be subjected to a pre-drying and/or heating, prior to the herein described acid treatment. Preferably the pre-drying and/or heating conditions are controlled in order to avoid damaging the natural polyphenols in the treated materials. For instance, the heating and/or pre-drying may assist in winnowing i.e., removing the shells from the cocoa beans.

In another embodiment, an additional step may be carried out which comprises reducing the size of the cocoa nibs by mechanical means before treatment with the acid or aqueous acidic solution. Techniques and apparatuses that can be applied for that purpose are well known in the art. This additional step has the benefit of expediting the processing and/or drying of the nibs.

The present invention also relates to red or purple cocoa-derived material obtained from cocoa beans that have been fermented with a microbial composition as defined herein wherein said cocoa-derived material is selected from the group comprising or consisting of cocoa nibs, cocoa flakes, cocoa cake, cocoa powder, cocoa liquor and chocolate, and preferably is cocoa nibs or cocoa liquor.

The colour of the cocoa-derived material such as cocoa nibs or cocoa liquor obtained in accordance with the invention, can be measured or determined using well known techniques. A suitable technique has been described above.

For instance, the colour of cocoa powders can be specified by means of colour coordinates. A frequently used system has been developed by R. S. Hunter (see Hunter, R. S., *The Measurement of Appearance*, John Wiley and Sons, New York, 1975). In this system, colour may be described in terms of coordinates $L^*$, $a^*$ and $b^*$, $C^*$ and $h°$. The L coordinate is consistent with the Value of Lightness, and from the $a^*$ and $b^*$ coordinates, the Chroma and Hue can be calculated. The $L^*$-coordinate can assume values between 0 (black) and 100 (white). The lower the L-value, the closer $L^*$ gets to zero, the darker the cocoa powder will appear. A high value of the $a^*$-coordinate indicates a pronounced red component in the colour of the cocoa powder; a high value of the $b^*$-coordinate points to the presence of a lot of yellow. With regard to the red colour, the higher the ratio $a^*:b^*$, the more red the colour of the cocoa will be. $C^*$ refers to the saturation of colour and $h°=arctg\ b^*/a^*$, is the hue value.

Appropriate measuring systems and apparatuses known in the art may be used to determine values of the colour coordinates. The L-, a- and b-values of cocoa powder may for example be determined, with the Hunterlab Digital Colour Difference Meter, type D 25 D2 A.

The term "red", as defined herein, preferably means that the cocoa-derived material, as defined above, when in the form of a powder (optionally after having been defatted), has
- an $L^*$ value comprised between 39 and 48, preferably between 40 and 45, more preferably between 40 to 43, most preferably between 40 to 42,
- an $a^*$ to $b^*$ ratio of greater than 1.6, such as greater than 1.8, more preferably greater than 2.0, and for instance comprised between 2.2 and 3.2, or between 2.4 and 3.1,
- a $C^*$ value of greater than 22, preferably greater than 25, and for instance comprised between 25 and 34, or between 28 and 33, or between 30 and 33, and
- a $h°$ value of comprised between 16 and 32, and for instance between 17 and 30, or between 17 and 25, as measured according to the above method.

Alternatively, the term "red" preferably means that
- the $L^*$ value is comprised between 40 and 57, preferably between 42 and 52 more preferably between 44 and 48,
- the $C^*$ value is comprised between 18 and 40, preferably between 25 and 35, more preferably between 18 and 30,
- an $h°$ value comprised between 7 and 40, preferably comprised between 10 and 35, more preferably greater than 7, and
- optionally an $a^*$ to $b^*$ ratio comprised between 1 and 8, preferably comprised between 3 and 6, more preferably from 4 to 5, as measured according to the above method.

The term "purple", as defined herein, preferably means that the cocoa-derived material, as defined above, when in the form of a powder (optionally after having been defatted), has
- an $L^*$ value of greater than 46, preferably comprised between 47 and 57, more preferably comprised between 48 and 56, most preferably comprised between 50 and 56, such as from 52 to 56,
- optionally an $a^*$ to $b^*$ ratio of less than 2.3, such as less than 1.8, more preferably comprised between 1 and 2.1, such as from 1.5 to 2.1,
- a $C^*$ value of less than 18, preferably comprised between 10 and 17, such as from 11 to 15, and
- a $h°$ value comprised between 20 and 50, preferably comprised between 25 and 40 or between 25 and 30, as measured according to the above method.

It shall be clear that the terms "red" and "purple" may also be considered to encompass other shades of these colours in substantially the same wavelength, such as for instance pink, mauve, violet and parme.

The present invention thus provides a cocoa-derived material as defined above in the form of a powder and having an $L^*$ value, a $C^*$ value, an $h°$ value, and optionally an $a^*$ to $b^*$ ratio as defined above. In an example the invention provides defatted cocoa liquor in the form of powder and having the coordinate values as given in table 2.

TABLE 2

| | Cocoa-derived material (defatted cocoa liquor) | | | |
|---|---|---|---|---|
| Coordinates | Example 1 | Example 2 | Example 3 | Example 4 |
| L* value | Between 40 and 45 | between 40 and 57 | between 47 and 57 | between 47 and 57 |
| C* value | between 28 and 33 | Between 18 and 40 | Between 10 and 17 | Less than 18 |
| h° value | between 17 and 25 | Between 7 and 40 | Between 20 and 50 | Between 25 and 40 |
| a* to b* ratio (optional) | Between 2.2 and 3.1 | Between 1 and 8 | Less than 2.3 | Between 1 and 2.1 |

Downstream Products

Cocoa products or cocoa-derived materials as defined herein and obtained according to methods of the present invention can be introduced in food products. The high-flavoured cocoa beans according to the invention are particularly suitable for the production of high-flavoured food products.

By using a well-defined microbial composition, it becomes possible to obtained fermented cocoa beans and cocoa-derived materials having particular taste, flavour, nutritional and/or organoleptic characteristics.

For instance, in an embodiment, the present invention permits to provide fermented cocoa beans and cocoa-derived materials which are less astringent and less bitter.

Also, the present invention permits to provide fermented cocoa beans and cocoa-derived materials having a strong aromatic taste. Therefore the cocoa beans and cocoa-derived materials are particularly suitable to be mixed with "dull" tasting cocoa materials.

In another embodiment, by using a well-defined microbial composition according to the invention, it becomes possible to yield cocoa beans and cocoa-derived materials with a fruity taste, e.g. with a taste of beer, banana, citrus, raspberry, etc. . . . , without having to add at any processing stage synthetic or natural flavour additives and/or plant/fruit materials or plant/fruit extracts.

In yet another embodiment, by using well-defined microbial strains in the microbial compositions used to ferment the beans, cocoa fermentation permits in some cases to increase vitamin content in the fermented beans, e.g. of vitamin B12.

In still another embodiment, y using well-defined microbial strains in the microbial compositions used to ferment; cocoa beans can be provided of which the shell has at least partly been degraded. Advantageously, such cocoa beans are easier to process and therefore provide higher yields of cocoa liquor. It is unexpected that such feature can be achieved by using a well-defined microbial composition to ferment the beans.

The invention further provides a food product, preferably a chocolate product, prepared with one or more cocoa beans and/or with one or more cocoa products or cocoa-derived materials as defined herein and to various uses of such food product.

Food products, e.g. chocolate or chocolate products, comprising cocoa beans or cocoa products or cocoa-derived materials derived thereof as defined herein have improved characteristics, including for instance improved storage stability, improved organoleptic properties such as for instance a better flavour profile, better flavour release, prolonged flavour retention and improved appearance, than equivalent products made from cocoa beans that have not been pre-treated in accordance with the present invention. The term "chocolate" as used herein intends to include dark chocolate, milk chocolate or white chocolate. The term "chocolate products" refers to a product containing chocolate as defined herein.

For instance, using the present fermented beans in the preparation of chocolate products has particular benefits and provides unexpected effects.

For example, in an embodiment, starting from fermented beans according to the invention, high flavanol-rich milk chocolate with a fine taste can be produced. In accordance with the invention, polyphenols are much better preserved in the cocoa beans when applying a controlled fermentation process as described herein. The amount of flavanols may even be 1.5 to 2 times higher than in conventional milk chocolate. Polyphenols are known to give an astringent taste. However, surprisingly, when using fermented beans according to the invention, which are very tasty and aromatic, astringency due to a high polyphenol content can be sufficiently masked by the nice flavour of the beans.

In another embodiment, the present invention permits to provide dark chocolate with a light colour and high cocoa taste. This type of chocolate can be obtained thanks to the light-breaking effect of beans that have been fermented using a microbial composition as described herein, i.e. because the beans have a light brown appearance. The present invention permits to provide cocoa beans from a non-Java origin, that nevertheless have L and a/b colour coordinate values (as explained above) that are similar to cocoa beans of a Java origin. Java beans generally have a lighter colouration genotype.

Cocoa powder that has been prepared from beans fermented according to the invention is a good tasting powder that is however lighter in colour than conventional cocoa powder. This type of "'lighter" powder can advantageously be mixed with dark-coloured cocoa powder that typically also has a high polyphenol content. The obtained cocoa powder mixture can then be used to prepare food products, in particular beverages or drinks, which despite a lighter colour have a high polyphenol content.

In yet another embodiment, a good and natural tasting cocoa butter can be prepared from beans fermented according to the invention. Typically cocoa butter is deodorized during its processing. Deodorization however has the disadvantage to induce losses of cocoa butter. Surprisingly, it was shown that when using cocoa beans fermented according to the invention to prepare cocoa butter significantly less deodorization of the cocoa butter is required.

In another embodiment, the present invention permits to provide a reproducible aromatic fine-flavoured chocolate in view of the reproducible and constant quality of the fermented beans. Moreover, even when starting from a relative uniform and reproducible fermented material to produce chocolate, a broad spectrum of tastes can be obtained. In fact, as a consequence of the excellent and controlled fermentation conditions as described herein, a lot of precursors are present in the fermented cocoa beans. These precursors can be optimally used by adjusting roasting conditions of the beans. In other words, the present invention permits to obtain a broad spectrum of different tastes essentially by adjusting the roasting conditions of the fermented beans.

A same effect applies when considering cocoa liquors. Even when starting from a relative uniform and reproducible fermented material to produce cocoa liquor, many different tastes of liquor can produced.

It should also be noted that the invention provides high quality cocoa butter, having lower amounts of FFA of other fat components compared to hitherto known cocoa butters.

The present invention will now be described in greater detail below with the aid of the examples which follow. It goes without saying, however, that these examples are given by way of illustration of the invention and do not constitute in any manner a limitation thereof.

EXAMPLES

Example 1

Use of a Microbial Composition According to the Invention to Ferment Cocoa Beans This example illustrates a method for fermenting cocoa beans using a microbial composition according to the invention as compared to a natural fermentation method. The microbial composition according to the invention used in this experiment comprised the following bacterial strains: *Lactobacillus plantarum, Lactobacillus fermentum, Acetobacter pasteurianus Lactobacillus parafarraginis*, and the yeast *Saccharomyces cerevisiae*.

For the beans fermented with a microbial composition according to the invention, unfermented Ivory Coast beans (e.g. 100 kg) were mixed with 100 ml microbial composition and after 2 days, turned and allowed to ferment for another 2 days. Other experimental conditions applied in the experiment are represented in table 3.

TABLE 3

| | experimental conditions | | |
|---|---|---|---|
| Conditions | Fermentation using a prior art starter culture comprising | Fermentation using a starter culture according to the invention comprising | Conventional fermentation Without starter culture |
| Microbial composition | Lactobacillus plantarum, Lactobacillus fermentum, Acetobacter pasteurianus Saccharomyces cerevisiae | Lactobacillus plantarum, Lactobacillus fermentum, Acetobacter pasteurianus Lactobacillus parafarraginis Saccharomyces cerevisiae | na (*) |
| Origin of the cocoa beans | Ivory Coast (Forestaro) | Ivory Coast (Forestaro) | Ivory Coast (Forestaro) |
| Amount of inoculum added (CFU/g beans) | $10^6$/g beans | $10^6$/g beans | Na (*) |
| Time needed to ferment | 4 to 5 days | 4 days | 6 days |
| Amounts in the fermented beans of polyphenols | Folin = +/−3% | Folin = +/−4.5% | Folin = +/−1% |
| Fructose | +/−1.8 mg/g | +/−5.9 mg/g | +/−3.5 mg/g |
| Glucose | +/−12 mg/g | +/−1.9 mg/g | +/−1.25 mg/g |
| Mannitol | +/−8 mg/g | +/−0.7 mg/g | +/−0.17 mg/g |
| Lactic acid | +/−5 mg/g | +/−1 mg/g | +/−1.32 mg/g |
| Citric acid | +/−5 mg/g | +/−4.9 mg/g | +/−6.21 mg/g |
| Acetic acid | +/−10 mg/g | +/−6.1 mg/g | +/−11.55 mg/g |
| Ethanol | +/−10 mg/g | +/−0.1 mg/g | Not detected |
| Microbial count | +/−$10^6$/g | +/−$10^4$/g | +/−$10^9$/g |

(*) na: not applicable
In a preferred example, the microbial composition according to the invention comprised $10^5$ CFU/g beans of each microbial strain.

Bean Composition

Results of this example illustrate that the fermentation of cocoa beans with the use of a microbial composition as defined herein is much faster than a conventional fermentation process, and that unexpectedly despite this faster fermentation, the amount of components in the fermented beans including their amounts of sugars, acids, etc, remains satisfactory and comparable to those found in conventionally fermented beans (see table 3).

Moreover, the results indicate that beans fermented with a microbial composition according to the invention have a much higher amount of polyphenols compared to conventionally fermented beans or compared to beans that have been fermented using a prior art starter culture.

Bean Appearance and Quality

Regarding the appearance of the obtained beans the following was noted. Surprisingly, the beans that were fermented using a microbial composition according to the invention showed a light-breaking effect. One speaks about a light-breaking effect in particular when the L value of the colour is 18 or higher, and preferably around 20 or higher. Surprisingly, this light-breaking effect was not observed with the conventionally fermented beans or with the beans that have been fermented using a prior art starter culture. Another particularly beneficial effect of using a microbial composition according to the invention for fermenting cocoa beans is that a lower microbial count is obtained compared to conventionally fermented beans or to beans that have been fermented using a prior art starter culture. In other words the amount of bacteria remaining on cocoa beans that were fermented according to the present invention was lower than on conventionally fermented cocoa beans (fermented for 6 days) or on beans that have been fermented using a prior art microbial composition for 4 days. This is advantageous, as in such case the beans fermented according to the present invention need to undergo less de-bacterisation to remove bacterial contamination before being further processed and/or can be less severely roasted.

In addition, the following quality analyses were performed: appearance of beans, cut test (index of fermentation), and sensorial analysis. The level of fermentation in the dried cocoa bean is typically determined by the "cut test". The cut test, which is an index of fermentation and relies on changes in colour, is the standard test used to assess the suitability of cocoa beans for chocolate manufacture. A total of 300 g beans were cut lengthwise through the middle to expose the maximum cut surface of the cotyledons. Both halves were examined in full daylight and placed in one of the following categories: fully brown (fermented); partly brown, partly purple (partly fermented); purple (not fermented, however, see below); slaty (over-fermented); insect damaged; moldy; or germinated.

Results of the cut test performed on the three types of beans are summarized in Table 4 and showed that the beans that were fermented using a microbial composition according to the invention showed less defects and were much more uniform than the two other types of beans. In table 4, slaty refers to beans with a grayish colour, and other defects include inter alia spores of insect or worm infestation and the bean count refers to the number of beans in a sample of 300 grams.

TABLE 4

| Observation | Fermentation using a prior art starter culture | Fermentation using a starter culture according to the invention | Conventional fermentation Without starter culture |
|---|---|---|---|
| Mould | 0 | 0 | 3 |
| Germinated | 0 | 0 | 1 |
| Slaty | 3 | 0 | 3 |
| Purple | 11 | 15 | 10 |
| Other defects | 2 | 0 | 5 |
| Bean count | 95 | 95 | 95 |

Results of a further cut test performed on cocoa beans fermented in another experiment using the present starter culture are summarized in Table 4a, side-by-side with select criteria applicable for so-called "Grade 1" beans. Note that Grade 1 beans are highly desirable and in short supply (e.g., they may often constitute only about 0.4% of total bean harvest). Advantageously, in a number of relevant quality parameters, such as the fraction of defective, mouldy or slaty beans, the beans fermented as taught herein are clearly superior even to Grade 1 beans. In this connection, one shall understand that bean count may be influenced less by fermentation than by season.

Also notably, as follows from Tables 4 and 4a the beans fermented as taught herein may contain a considerably greater fraction of purple beans than conventionally fermented beans. Although the parameter "purple" may normally suggest beans that are not adequately fermented, this is not the case here. In particular as explained above the colour of beans obtained by fermentation as taught herein is lighter (paler) than that of conventionally fermented beans. In fact, the beans scored as "purple" in the cut test of Table 4a are well-fermented, as determined by examination of their structure or texture (not shown). Hence, the increased "purple" score reflects the advantageous light colouration of our beans.

TABLE 4a

| Observation | Fermentation using a starter culture according to the invention | Grade 1 criteria |
| --- | --- | --- |
| Bean count | 93 | 100 |
| Defects | 1.43 | 3.00 |
| Mould | 0.48 | 3.00 |
| Slaty | 0.93 | 3.00 |
| Germinated | 0.25 | |
| Broken | 1.72 | <3 |
| FFA | 0.56 | |
| Purple | 42.54 | |
| Humidity | 8.13 | 8 |

Example 2

Taste Experiments on Cocoa Beans

The beans that were fermented using a microbial composition according to the invention and the conventionally fermented beans as described in example 1 were subjected to taste analyses.

The beans prepared as described in Table 3 above, were then dried by evaporation of the water under vacuum during gentle heating, at a temperature below 60° C., until the moisture content was less than 10%. Then the beans were roasted in an oven at 120° C. for 30 min. The flavours generated by the roasting were then evaluated by a panel of at least 5 individuals used to evaluating such flavours. Scores were assessed on a point system from 0 to 5. A high score in a category indicated a strong intensity of a particular flavour. Each sample was evaluated for the following sensations: "acidity"; "astringency"; "bitterness"; "chocolate"; "fruity"; "Aromatic"; "wine", "earthy"; "mouldy"; "smoky"; "baggy" (i.e. off flavours). Table 5 and FIG. 1 show the results of a taste panel for the beans as prepared according to this example.

According to the objective taste panel, the beans fermented according to a method of the invention had a reproducible and good quality, for instance comparable to "JAVA" origin characteristics. The results indicate that unexpectedly an acceptable taste and quality could be obtained even if the beans were easily and rapidly obtained, i.e. in about 4 days, which is considerably faster than when applying a conventional fermentation process. Moreover, compared to conventionally beans, the beans fermented according to a method of the invention had lower scores for off flavours, such as earthy; mouldy; smoky; baggy.

TABLE 5

| Descriptors | Fermentation using a starter culture according to the invention Judges Average | Conventional fermentation Without starter culture Average |
| --- | --- | --- |
| Acidity | 1.5 | 1 |
| Astringency | 1.75 | 2 |
| Bitterness | 2.25 | 2.25 |
| Chocolate | 0.75 | 0.25 |
| Fruity | 0.5 | 0 |
| Aromatic | 0.25 | 0 |
| wine | 0 | 0 |
| Earthy | 0 | 1 |
| Mouldy | 0 | 1 |
| Smoky | 0 | 0 |
| baggy | 0 | 1 |

Example 3

Taste Experiments on Chocolate

Figure 2:
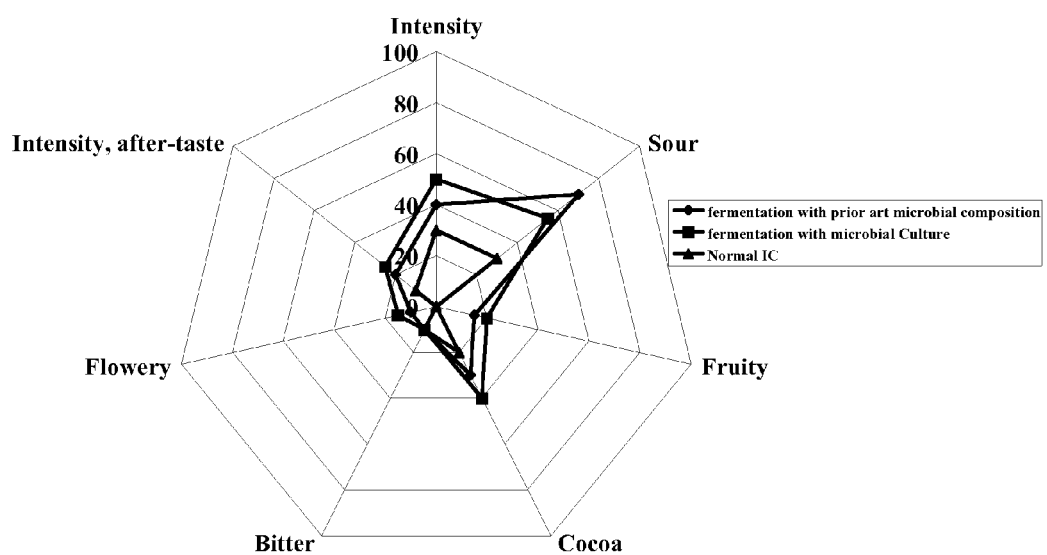
FIG. 2 shows the results of a taste panel experiment conducted on i) chocolate prepared from naturally fermented cocoa beans; ii) chocolate prepared from cocoa beans that have been fermented by using a prior art starter culture; and iii) chocolate prepared from cocoa beans that have been fermented by using a starter culture according to the invention.

The beans described in example 1 were used to prepare chocolate. The obtained chocolate contained 52% of cocoa solids and was subjected to a taste panel of at least 5 individuals which assessed the obtained chocolate on a scale from 0 to 100 for the following sensations: "intensity"; "bitterness"; "cocoa flavour"; "fruity"; "sour"; "flowery"; "intensity of aftertaste". FIG. 2 shows the results of this taste experiment.

As can also been derived from FIG. 2 and as was reported by the taste panel, chocolate prepared with beans that were fermented using a microbial composition according to the invention had a very homogeneous taste and no perceivable off-flavours, and had improved fruity and flowery taste.

In contrast thereto, chocolate prepared with the conventionally fermented beans or with the beans fermented with the indicated microbial composition tasted less fruity and less flowery. Also, the chocolate prepared with the beans fermented with the indicated microbial composition taste more sour.

Also, chocolate prepared with beans that were fermented using a microbial composition according to the invention also were reported to have high amounts of polyphenols.

Example 4

Cocoa Beans Fermented Using a Microbial Composition According to the Present Invention In this example, beans were fermented in boxes. 100 kg of unfermented cocoa beans from Ivory Coast (variety Forestaro) were mixed with 100 ml microbial composition mixture comprising the following bacterial strains: *Lactobacillus plantarum, Lactobacillus fermentum, Acetobacter*

*pasteurianus*, and *Lactobacillus parafarraginis*; and the yeast *Saccharomyces cerevisiae* and left to ferment for 2 days. After 2 days, the beans were turned and allowed to further ferment for another 2 days.

During the fermentation pH and temperature were followed up online, and dried fermented beans were recovered after 4 days. pH and temperatures can be measured by using a digital sensor (e.g. pH 340i sensor, WTW Gmbl, Weilheim, Germany) that was placed in the middle of the fermenting biomass in the boxes.

The beans were then dried (e.g. by sun drying). Then the dried beans were roasted at 2 at 120° C. for 30 min.

For comparison, unfermented cocoa beans from Ivory Coast (variety Forestaro) were conventionally fermented for 6 days and dried and roasted in a same way as described above.

The following features were measured: end pH, total polyphenol content, fat content, content of free fatty acids (FFA), cut test, colour and taste of cocoa mass.

The Applicants determined that fermenting cocoa beans using a microbial composition as defined herein had the beneficial effect of improving processing of the beans. The obtained beans required inter alia less labour intensive drying. Also, there was no mould growth during drying and clean beans were obtained after drying. Moreover, the obtained beans had a nice brown colour, indicating that they had been suitable fermented.

Figure 3:
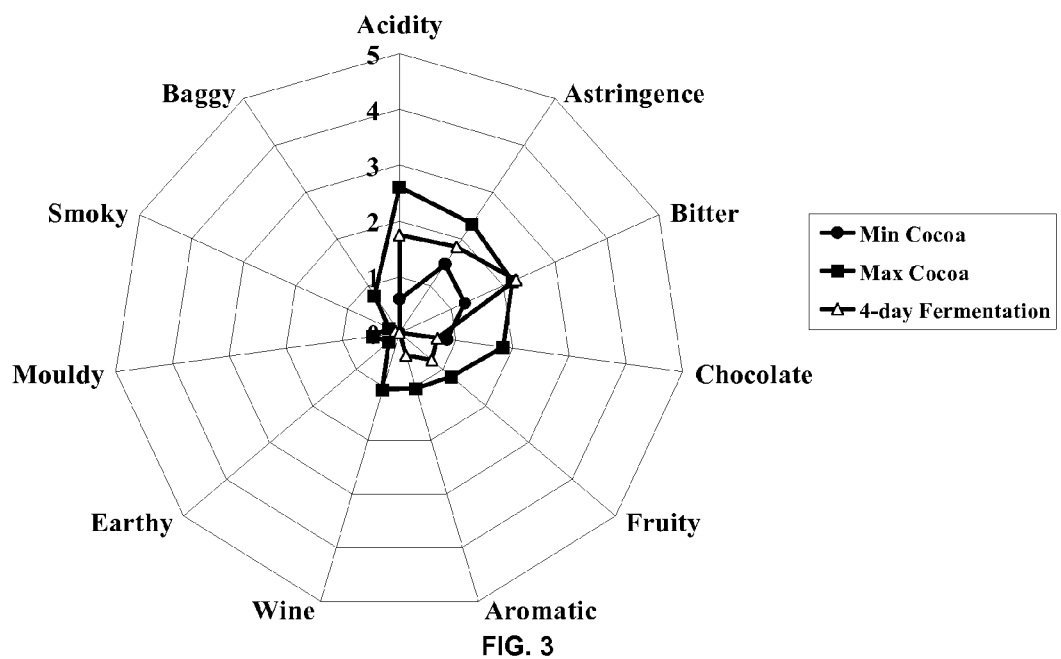
FIG. 3 shows the results of a taste panel experiment conducted on samples of cocoa beans that have been fermented by using a microbial composition according to the invention as compared to standard minimum and maximum acceptable taste ranges for cocoa.

FIG. 3 shows the results of the taste panel experiment, and indicates that the cocoa beans that had been subjected to fermentation with a microbial composition as defined herein for 4 days obtained a good taste, which was comprised within the minimum and maximum acceptable cocoa taste ranges. As illustrated on FIG. 3 and according to an objective taste panel, the obtained beans had a good flavour without any off-taste present, even if the beans could be obtained in a shortened fermentation time (e.g. 4 days).

Figure 4:
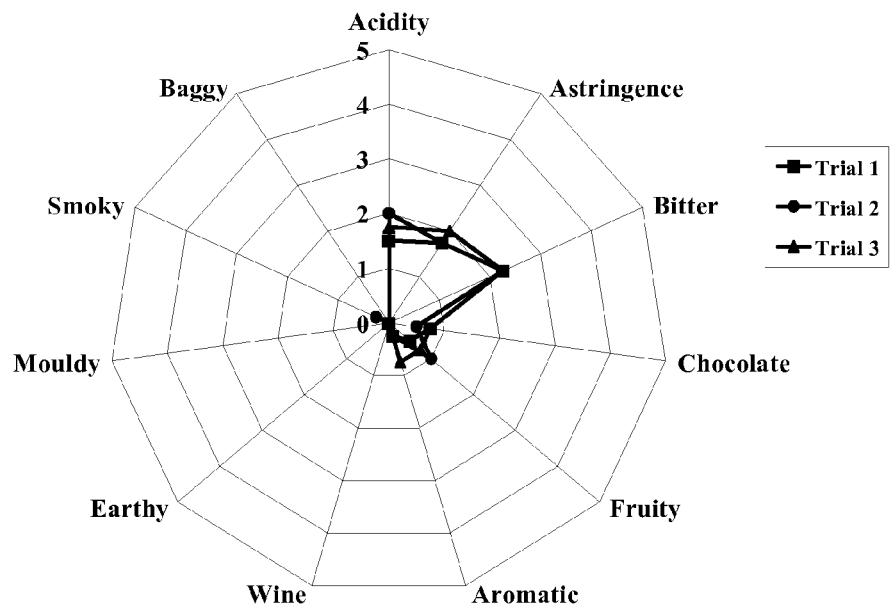
FIG. 4 shows the results of a taste panel experiment conducted on samples of cocoa beans that have been fermented by using a microbial composition according to the invention and obtained in three different trials.

FIG. 4 compares the results of the taste panel experiment carried out on three different samples of beans that have each been fermented with a microbial composition as defined herein for 4 days. As can be seen, each trial yielded cocoa beans with a good taste, which felt within the minimum and maximum acceptable cocoa taste ranges. Referring to FIG. 4, it can be concluded that the present method and the taste of obtained beans is highly reproducible.

FIGS. 3 and 4 also illustrate that the use of a microbial composition as defined herein provides beans of a reproducible and good quality and that good tasting cocoa mass can be obtained after only 4 days of fermentation, and that in this example no substantially off flavours where detected in three separate trials.

Furthermore, the Applicants have shown that the content of FFA was much lower in the beans that had been fermented using a microbial composition according to the invention compared to conventionally fermented beans. In spontaneously fermented beans FFA values more than 8% were measured, while in beans fermented using a microbial composition according to the invention FFA levels between 0.3 and 0.6% (±0.3%) were measured.

In addition, with regard to defects, the Applicants have determined that in spontaneous fermentation more than 4% defects, e.g. flats beans, infected beans, etc, were detected, while in dried beans fermented using a microbial composition according to the invention less then 0.5% defects were detected.

Figure 5:
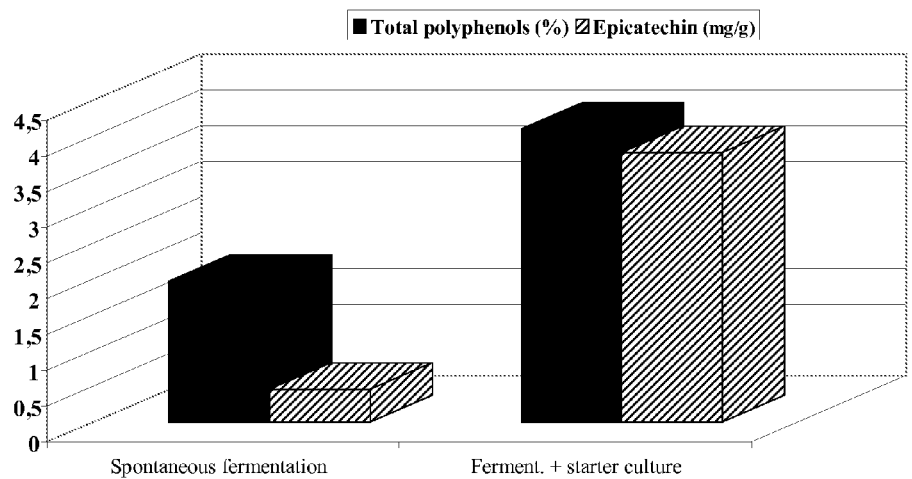
FIG. 5 shows the results of a polyphenol and epicatechin levels in cocoa beans that have been subjected to a natural fermentation process as compared to cocoa beans that have been fermented by using a microbial composition according to the invention. On FIG. 5 the polyphenols are expressed in % and the epicatechin is expressed in mg/g.

Also, FIG. 5 shows that much higher amounts of polyphenols in general (expressed in %) and of epicatechin in particular (expressed in mg/g) were measured in beans that had been fermented using a microbial composition according to the invention compared to conventionally fermented beans. In particular, as shown on FIG. 5 there was a two times higher preservation of the natural polyphenol content and a high increase in epicatechin content in the dried beans fermented using a microbial composition according to the invention as compared to conventionally fermented and dried beans.

Figure 6:
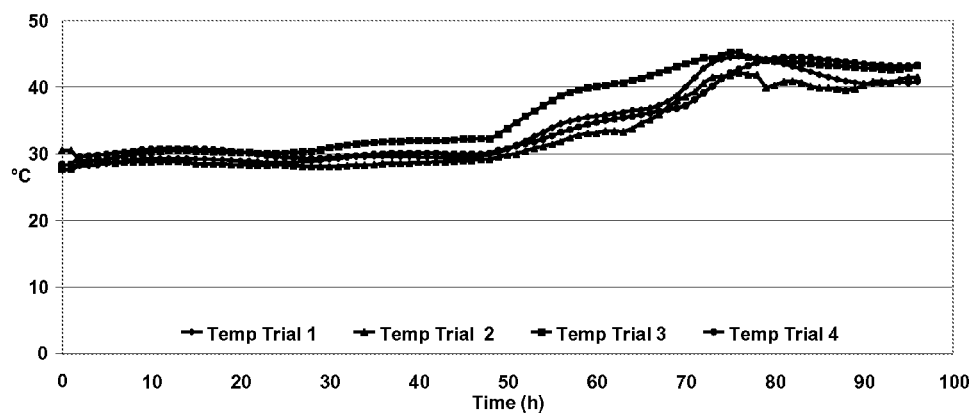
FIG. 6 shows the results of temperature profiles during the fermentation of cocoa beans that are fermented by using a microbial composition according to the invention in four different trials.

Finally, the Applicants showed that similar results could be obtained independent of the applied fermentation method (e.g. in box, heap, basket). All methods led to the same end results and quality. There were no substantial bean defaults, and beans were of excellent quality, whatever the fermentation method applied. Also, as indicated in FIG. 6 for a heap basket fermentation, when carrying out four different trials, temperature and pH profiles of the fermentation were highly reproducible.

Summarised, by using a microbial composition as defined herein for steering the fermentation of cocoa beans, fermented beans can be obtained having the following features:
- beans that are clean and easier to store; without substantial defects; no substantial fungal growth detected; no significant germination;
- Contain few free fatty acids (FFA-values below 0.5 wt %);
- High quality beans with good processability of beans;
- Reproducible aromatic taste with no significant off-flavour.

Example 5

Appearance of Cocoa Beans Fermented Using a Microbial Composition According to the Present Invention Cocoa beans were fermented under similar conditions as explained in Example 1. The obtained fermented beans showed a light-breaking effect. Surprisingly, this light-breaking effect was not observed with the conventionally fermented beans. Table 6 illustrates the coordinate values according to the Hunter colour system for a sample of cocoa beans fermented according to the present invention as compared to a sample of cocoa beans that has been conventionally fermented, without using a microbial composition as defined herein.

TABLE 6

| Cocoa beans | % fat | % FFA | L* | a* | b* | C* | h° | pH | Viscosity |
|---|---|---|---|---|---|---|---|---|---|
| Fermented using microbial composition according to the invention | 56.13 | 0.45 | 19.97 | 13.54 | 13.74 | 19.29 | 45.42 | 5.34 | 41.5 |
| Conventionally fermented | 55.56 | 1.35 | 14.63 | 13.03 | 13.77 | 18.96 | 46.58 | 5.84 | 67.8 |

From these results it is clear that the L-value is significantly different and higher for the beans fermented according to the invention compared to the conventionally fermented beans. Processing of the fermented beans according to the invention into chocolate may therefore lead to lighter chocolate, for which there is a high demand in the chocolate industry and by customers. For comparison, the L values obtained for beans fermented according to the invention are comparable to those of Java beans, which are traditionally known to have lighter colour and to be around 20. In a typical example, the values for Java beans are the following: L=20, a=17, b=20.

Example 6

Processability of Cocoa Beans Fermented Using a Microbial Composition According to the Present Invention The inventors have additionally realised that beans fermented as taught herein allow for numerous improvements in the downstream processing of the beans, such as when using conventional Buhler or Barth lines. In an pilot trial using a Barth line the overall process efficiency could be increased up by 30 to 50% compared to conventionally fermented beans, with concomitant reductions in energy and maintenance costs. This overall rise in process efficiency comprises improvements at the individual stages of the downstream processing. For example, the process speed of micronising and winnowing could be increased by about 28%, process speed of mixing and roasting could each be improved by about 100% with room for further optimisation, while the process speed of cooling could be improved by about 200%. In this trial, grinding could be improved by about 30-40%.

Moreover, beans fermented as taught herein may also provide for faster liquor pressing. Additionally, beans fermented as taught herein may provide for improved chocolate rheology, which in turn allows to reduce the amount of cocoa butter in chocolate products, thereby reducing the cost.

The inventors have also noted considerable improvements in the grinding process output as shown in Tables 7 and 8 (see average and maximum output values) for respectively a Barth and Bühler lines.

TABLE 7

| | Output average | Fineness | Output maximum |
|---|---|---|---|
| Filling (beans from conventional fermentation without starter culture) | | | |
| 130936 | 1933 | 99.81% | 1933 |
| 140939 | 1785 | 99.86% | 1827 |
| 130942 | 1490 | 99.80% | 1762 |
| 140944 | 1230 | 99.90% | 1768 |
| 130945 | 1802 | 99.80% | 1802 |
| 140947 | 1801 | 99.80% | 1887 |
| 130948 | 1500 | 99.84% | 1886 |
| 140951 | 1365 | 99.82% | 1782 |
| 130953 | 1400 | 99.81% | 1665 |
| Average | 1590 | 99.83% | 1812 |
| Filling (beans from fermentation using a starter culture according to the invention) | | | |
| 130930 | 1423 | 99.83% | 2385 |
| 130926 | 2097 | 99.83% | 2270 |
| 130923 | 1459 | 99.83% | 1772 |

TABLE 7-continued

| | Output average | Fineness | Output maximum |
|---|---|---|---|
| 140933 | 1486 | 99.80% | 2402 |
| 140928 | 1713 | 99.79% | 2543 |
| 140925 | 1715 | 99.81% | 2461 |

TABLE 8

| | Output average | Fineness | Output maximum (kg/h) |
|---|---|---|---|
| Filling (beans from conventional fermentation without starter culture) | | | |
| 320831 | 3281 | 99.12% | 3659 |
| 320828 | 2868 | 99.06% | 3405 |
| 320825 | 3493 | 98.64% | 3493 |
| 310830 | 2953 | 99.16% | 3442 |
| 310827 | 3170 | 99.26% | 3170 |
| 330829 | 3386 | 98.89% | 3412 |
| 330826 | 3398 | 98.98% | 3398 |
| 330824 | 2560 | 98.58% | 3468 |
| 330832 | 3209 | 99.05% | 3542 |
| Average | 3146 | 98.97% | 3443 |
| Filling (beans from fermentation using a starter culture according to the invention) | | | |
| 310847 | 3600 | 98.71% | 4350 |
| 330848 | 3290 | 99.22% | 3990 |
| 320849 | 3785 | 98.94% | 4525 |
| 310850 | 4365 | 99.29% | 4630 |
| 330851 | 4270 | 99.48% | 4270 |
| 320852 | 4245 | 99.52% | 4455 |
| 310853 | 4285 | 99.25% | 4420 |
| 320854 | | 99.52% | |
| 330855 | 4450 | 99.16% | 4450 |
| 310856 | 4280 | 99.18% | 4280 |
| 320857 | 3630 | 98.98% | 3770 |
| Average | 4020 | 99.20% | 4314 |

Example 7

Experiments Using Other Microbial Compositions of the Invention

Cocoa fermentation is carried out under the general conditions of Example 1, except that microbial cultures are employed comprising the following bacterial and yeast strains.

Composition I: *Lactobacillus plantarum, Lactobacillus fermentum, Acetobacter pasteurianus, Lactobacillus farraginis, Saccharomyces cerevisiae.*

Composition II: *Lactobacillus plantarum, Lactobacillus fermentum, Acetobacter pasteurianus Lactobacillus diolivorans, Saccharomyces cerevisiae.*

Composition III: *Lactobacillus plantarum, Lactobacillus fermentum, Acetobacter pasteurianus Lactobacillus faeni, Saccharomyces cerevisiae.*

Composition IV: *Lactobacillus plantarum, Lactobacillus fermentum, Acetobacter pasteurianus Lactobacillus paracasei, Saccharomyces cerevisiae.*

Composition V: *Lactobacillus plantarum, Lactobacillus fermentum, Acetobacter pasteurianus Lactobacillus parafarraginis, Lactobacillus farraginis, Saccharomyces cerevisiae.*

Composition VI: *Lactobacillus plantarum, Lactobacillus fermentum, Acetobacter pasteurianus Lactobacillus parafarraginis, Lactobacillus diolivorans, Saccharomyces cerevisiae.*

The beans fermented using starter compositions I to VI are examined and advantages comparable to those seen using the microbial composition of Example 1 as illustrated in Examples 2 to 6, are observed. In particular, beans fermented using starter compositions I to VI also allow for controlling the index of fermentation of cocoa beans (cut test criteria, colouration), appearance and/or sensorial properties of the fermented beans, e.g., sensorial properties, organic acids, sugar alcohols, polyphenol, theobromine, or caffeine content of roasted beans, and/or organoleptic characteristics (taste, flavour, aroma, texture, colour, rheology, crystallisation behaviour, etc.), nutritional characteristics, technological properties, quality assets (aroma, taste, flavour, fatty acid composition, polyphenol content, theobromine content, caffeine content, etc.) of cocoa products, such as, particularly chocolate. Beans fermented using starter compositions I to VI also display light-breaking effect comparable to that set out in Example 5 and improved processing analogous to that taught in example 6.

The invention claimed is:

1. A Method for regulating fermentation of plant material essentially consisting of beans and/or pulp derived from fruit pods of the species *Theobroma cacao*, said method comprising adding to the plant material a microbial composition comprising:
   *Lactobacillus plantarum, Lactobacillus fermentum, Acetobacter pasteurianus, Lactobacillus parafarraginis*, and
   at least one strain of a yeast species of a genus selected from the group consisting of *Saccharomyces* and *Candida*.

2. The method according to claim 1, wherein said microbial composition further comprises at least one additional *Lactobacillus* species selected from the group consisting of *Lactobacillus* farraginis, *Lactobacillus* diolivorans, *Lactobacillus faeni* and *Lactobacillus paracasei*.

3. The method according to claim 1, wherein said yeast is *Saccharomyces cerevisiae*.

4. The method according to claim 1, wherein said microbial composition is a starter culture or a high density culture, comprising at least $10^2$ CFU of bacterial strains per g plant material.

5. The method according to claim 1, wherein said microbial composition consists essentially of:
   Microbial Composition 1: *Lactobacillus plantarum, Lactobacillus fermentum, Acetobacter pasteurianus, Lactobacillus parafarraginis, Lactobacillus farraginis, Saccharomyces cerevisiae*, or,
   Microbial Composition 2: *Lactobacillus plantarum, Lactobacillus fermentum, Acetobacter pasteurianus, Lactobacillus parafarraginis, Lactobacillus diolivorans, Saccharomyces cerevisiae*.

6. The method according to claim 1, wherein said microbial composition comprises between $10^3$ and $10^7$ CFU/g of plant material of each strain.

7. The method according to claim 1, wherein said microbial composition is a liquid culture, liquid pressed culture, frozen or dried form, freeze dried form and spray/fluid bed dried form, or frozen or freeze-dried concentrated.

8. The method according to claim 1, wherein said microbial composition is provided in a sealed enclosure.

9. The method according to claim 1, wherein said microbial composition further comprises buffering agents and growth stimulating agents or preservatives or carriers.

10. The method according to claim 1, wherein said plant material is of non-Java origin.

11. A Method for producing a red or purple cocoa-derived material from fermented beans, comprising the steps of:
   a) providing cocoa beans that have been fermented with a microbial composition comprising:
      *Lactobacillus plantarum, Lactobacillus fermentum, Acetobacter pasteurianus, Lactobacillus parafarraginis*, and
      at least one strain of a yeast species of a genus selected from the group consisting of *Saccharomyces* and *Candida*,
   b) preparing a cocoa-derived material from the fermented beans of step a), and
   c) treating the cocoa-derived material of step b) with an acid or with an aqueous acidic solution, wherein said cocoa-derived material is selected from the group comprising cocoa nibs, cocoa flakes, cocoa cake, cocoa powder, cocoa liquor and chocolate, and preferably cocoa nibs or cocoa liquor.

12. The method according to claim 11, wherein said microbial composition further comprises at least one additional *Lactobacillus* species selected from the group consisting of *Lactobacillus farraginis, Lactobacillus diolivorans, Lactobacillus faeni* and *Lactobacillus paracasei*.

13. The method according to claim 11, wherein said yeast is *Saccharomyces cerevisiae*.

14. The method according to claim 11, wherein said microbial composition is a starter culture, comprising at least $10^2$ CFU of bacterial strains per g plant material.

15. The method according to claim 11, wherein said microbial composition consists essentially of:
   Microbial Composition 1: *Lactobacillus plantarum, Lactobacillus fermentum, Acetobacter pasteurianus, Lactobacillus parafarraginis, Lactobacillus farraginis, Saccharomyces cerevisiae*, or,
   Microbial Composition 2: *Lactobacillus plantarum, Lactobacillus fermentum, Acetobacter pasteurianus, Lactobacillus parafarraginis, Lactobacillus diolivorans, Saccharomyces cerevisiae*.

16. The method according to claim 11, wherein said microbial composition comprises between $10^3$ and $10^7$ CFU/g of plant material of each strain.

17. The method according to claim 11, wherein said microbial composition is a liquid culture, liquid pressed culture, frozen or dried form, freeze dried form and spray/fluid bed dried form, or frozen or freeze-dried concentrated.

18. The method according to claim 11, wherein said microbial composition is provided in a sealed enclosure.

19. The method according to claim 11, wherein said microbial composition further comprises buffering agents and growth stimulating agents or preservatives or carriers.

20. The method according to claim 11, wherein said plant material is of non-Java origin.

* * * * *